United States Patent
Sibbitt, Jr. et al.

(10) Patent No.: US 8,048,108 B2
(45) Date of Patent: Nov. 1, 2011

(54) VASCULAR CLOSURE METHODS AND APPARATUSES

(75) Inventors: Wilmer L. Sibbitt, Jr., Albuquerque, NM (US); Randy R. Sibbitt, Helena, MT (US)

(73) Assignee: Abbott Vascular Inc., Santa Clara, CA (US)

( * ) Notice: Subject to any disclaimer, the term of this patent is extended or adjusted under 35 U.S.C. 154(b) by 62 days.

(21) Appl. No.: 12/365,397

(22) Filed: Feb. 4, 2009

(65) Prior Publication Data
US 2009/0254119 A1    Oct. 8, 2009

Related U.S. Application Data

(63) Continuation of application No. 11/316,775, filed on Dec. 23, 2005, now abandoned.

(51) Int. Cl.
*A61B 17/08* (2006.01)
*A61D 1/00* (2006.01)

(52) U.S. Cl. ....................................................... 606/213

(58) Field of Classification Search ................... 606/139, 606/140, 142, 144, 149, 151, 157, 213, 215, 606/216, 219–221, 232; 128/898
See application file for complete search history.

(56) References Cited

U.S. PATENT DOCUMENTS

| | | |
|---|---|---|
| 287,046 A | 10/1883 | Norton |
| 312,408 A | 2/1885 | Wackerhagen |
| 438,400 A | 10/1890 | Brennen |
| 597,165 A | 1/1898 | Hall |
| 659,422 A | 10/1900 | Shidler |
| 989,231 A | 4/1911 | Davis |
| 1,088,393 A | 2/1914 | Backus |
| 1,331,401 A | 2/1920 | Summers |
| 1,574,362 A | 9/1922 | Callahan |
| 1,596,004 A | 8/1926 | De Bengoa |
| 1,625,602 A | 4/1927 | Gould et al. |
| 1,647,958 A | 11/1927 | Ciarlante |
| 1,880,569 A | 10/1932 | Weis |
| 1,940,351 A | 3/1933 | Howard |
| 2,012,776 A | 8/1935 | Roeder |
| 2,087,074 A | 7/1937 | Tucker |
| 2,131,321 A | 10/1937 | Hart |

(Continued)

FOREIGN PATENT DOCUMENTS

FR    2768324    3/1999

(Continued)

OTHER PUBLICATIONS

U.S. Appl. No. 60/693,531, filed Jun. 24, 2005, Carly.

(Continued)

*Primary Examiner* — Corrine M McDermott
*Assistant Examiner* — Dianne Dornbusch
(74) *Attorney, Agent, or Firm* — Workman Nydegger; Randy Shen

(57) ABSTRACT

A vascular closure device comprised of a sheath-delivered expandable, umbrella-like device with structural radial members with terminal and non-terminal hooks that engage the vessel wall. Unlike other vascular closure umbrella-type devices that effect closure by opening of the umbrella to cover an opening, the present invention effects closure of the aperture with closure of the umbrella. The closure can be maintained by a retainer lock that slides down the members, causing contraction, bringing the members into a compressed configuration (e.g., a parallel orientation of linear members) and the wound edges together, permitting immediate vascular closure and healing of the blood vessel. The device can be delivered and recovered by an intravascular sheath.

27 Claims, 12 Drawing Sheets

U.S. PATENT DOCUMENTS

| | | |
|---|---|---|
| 2,108,206 A | 2/1938 | Meeker |
| 2,127,903 A | 8/1938 | Bowen |
| 2,254,620 A | 9/1941 | Miller |
| 2,316,297 A | 4/1943 | Southerland et al. |
| 2,371,978 A | 3/1945 | Perham |
| 2,397,823 A | 4/1946 | Walter |
| RE22,857 E | 3/1947 | Ogburn |
| 2,453,227 A | 11/1948 | James |
| 2,595,086 A | 11/1948 | Larzelere |
| 2,583,625 A | 1/1952 | Bergan |
| 2,588,589 A | 3/1952 | Tauber |
| 2,610,631 A | 9/1952 | Calicchio |
| 2,646,045 A | 7/1953 | Priestley |
| 2,684,070 A | 7/1954 | Kelsey |
| 2,692,599 A | 10/1954 | Creelman |
| 2,910,067 A | 10/1959 | White |
| 2,941,489 A | 6/1960 | Fischbein |
| 2,944,311 A | 7/1960 | Schneckenberger |
| 2,951,482 A | 9/1960 | Sullivan |
| 2,959,172 A | 11/1960 | Held |
| 2,969,887 A | 1/1961 | Darmstadt et al. |
| 3,015,403 A | 1/1962 | Fuller |
| 3,033,156 A | 5/1962 | Verlish |
| 3,104,666 A | 9/1963 | Hale et al. |
| 3,113,379 A | 12/1963 | Frank |
| 3,120,230 A | 2/1964 | Skold |
| 3,142,878 A | 8/1964 | Santora |
| 3,197,102 A | 7/1965 | Bates et al. |
| 3,209,754 A | 10/1965 | Brown |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,482,428 A | 12/1969 | Kapitanov et al. |
| 3,494,533 A | 2/1970 | Green et al. |
| 3,523,351 A | 8/1970 | Filia |
| 3,586,002 A | 6/1971 | Wood |
| 3,587,115 A | 6/1971 | Shiley |
| 3,604,425 A | 9/1971 | Le Roy |
| 3,618,447 A | 11/1971 | Goins |
| 3,630,205 A | 12/1971 | Listner |
| 3,653,388 A | 4/1972 | Tenckhoff |
| 3,665,926 A | 5/1972 | Flores |
| 3,677,243 A | 7/1972 | Nerz |
| 3,757,629 A | 9/1973 | Schneider |
| 3,776,237 A | 12/1973 | Hill et al. |
| 3,802,438 A | 4/1974 | Wolvek |
| 3,805,337 A | 4/1974 | Branstetter |
| 3,814,104 A | 6/1974 | Irnich et al. |
| 3,820,544 A | 6/1974 | Semm |
| 3,828,791 A | 8/1974 | Santos |
| 3,840,017 A | 10/1974 | Violante |
| 3,856,016 A | 12/1974 | Davis |
| 3,874,388 A | 4/1975 | King et al. |
| 3,878,848 A | 4/1975 | Hiebert |
| 3,908,662 A | 9/1975 | Razgulov et al. |
| 3,918,455 A | 11/1975 | Coplan |
| 3,926,194 A | 12/1975 | Greenberg et al. |
| 3,939,820 A | 2/1976 | Grayzel |
| 3,944,114 A | 3/1976 | Coppens |
| 3,985,138 A | 10/1976 | Jarvik |
| 4,011,872 A | 3/1977 | Komiya |
| 4,014,492 A | 3/1977 | Rothfuss |
| 4,018,228 A | 4/1977 | Goosen |
| 4,064,881 A | 12/1977 | Meredith |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,162,673 A | 7/1979 | Patel |
| 4,168,073 A | 9/1979 | LaRue |
| 4,169,476 A | 10/1979 | Hiltebrandt |
| 4,182,339 A | 1/1980 | Hardy, Jr. |
| 4,185,636 A | 1/1980 | Gabbay et al. |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,216,776 A | 8/1980 | Downie et al. |
| 4,217,665 A | 8/1980 | Bex et al. |
| 4,217,902 A | 8/1980 | March |
| 4,235,177 A | 11/1980 | Arbuckle |
| 4,235,238 A | 11/1980 | Ogiu et al. |
| 4,278,091 A | 7/1981 | Borzone |
| 4,316,469 A | 2/1982 | Kapitanov |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,437,465 A | 3/1984 | Nomoto et al. |
| 4,440,170 A | 4/1984 | Golden et al. |
| 4,469,101 A | 9/1984 | Coleman et al. |
| 4,480,356 A | 11/1984 | Martin |
| 4,485,816 A | 12/1984 | Krumme |
| 4,492,229 A | 1/1985 | Grunwald |
| 4,493,323 A | 1/1985 | Albright et al. |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Vaillancourt |
| 4,526,174 A | 7/1985 | Froehlich |
| 4,553,543 A | 11/1985 | Amarasinghe |
| 4,586,503 A | 5/1986 | Kirsch et al. |
| 4,586,614 A | 5/1986 | Ger |
| 4,587,969 A | 5/1986 | Gillis |
| 4,592,498 A | 6/1986 | Braun et al. |
| 4,596,559 A | 6/1986 | Fleischhacker |
| 4,607,638 A | 8/1986 | Crainich |
| 4,610,248 A | 9/1986 | Rosenberg |
| 4,610,251 A | 9/1986 | Kumar |
| 4,610,252 A | 9/1986 | Catalano |
| 4,629,450 A | 12/1986 | Suzuki et al. |
| 4,635,634 A | 1/1987 | Santos |
| 4,651,733 A | 3/1987 | Mobin-Uddin |
| 4,655,211 A | 4/1987 | Sakamoto et al. |
| 4,665,906 A | 5/1987 | Jervis |
| 4,687,469 A | 8/1987 | Osypka |
| 4,693,249 A | 9/1987 | Schenck et al. |
| 4,702,250 A | 10/1987 | Ovil et al. |
| 4,719,917 A | 1/1988 | Barrows et al. |
| 4,723,549 A | 2/1988 | Wholey et al. |
| 4,724,840 A | 2/1988 | McVay et al. |
| 4,738,658 A | 4/1988 | Magro et al. |
| 4,738,666 A | 4/1988 | Fuqua |
| 4,744,364 A | 5/1988 | Kensey |
| 4,747,407 A | 5/1988 | Liu et al. |
| 4,748,982 A | 6/1988 | Horzewski et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,803,984 A | 2/1989 | Narayanan et al. |
| 4,830,002 A | 5/1989 | Semm |
| 4,832,688 A | 5/1989 | Sagae et al. |
| 4,836,204 A | 6/1989 | Landymore et al. |
| 4,836,205 A | 6/1989 | Barrett |
| 4,848,341 A | 7/1989 | Ahmad |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,898,155 A | 2/1990 | Ovil et al. |
| 4,902,508 A | 2/1990 | Badylak et al. |
| 4,911,164 A | 3/1990 | Roth |

| | | | | | | |
|---|---|---|---|---|---|---|
| 4,917,087 A | 4/1990 | Walsh et al. | | 5,209,756 A | 5/1993 | Seedhom et al. |
| 4,917,089 A | 4/1990 | Sideris | | 5,211,650 A | 5/1993 | Noda |
| 4,926,860 A | 5/1990 | Stice et al. | | 5,217,024 A | 6/1993 | Dorsey et al. |
| 4,929,240 A | 5/1990 | Kirsch et al. | | 5,217,470 A | 6/1993 | Weston |
| 4,929,246 A | 5/1990 | Sinofsky | | 5,217,471 A | 6/1993 | Burkhart |
| 4,934,364 A | 6/1990 | Green | | 5,217,485 A | 6/1993 | Liv et al. |
| 4,935,027 A | 6/1990 | Yoon | | 5,219,358 A | 6/1993 | Bendel et al. |
| 4,950,258 A | 8/1990 | Kawai et al. | | 5,222,974 A | 6/1993 | Kensey et al. |
| 4,950,285 A | 8/1990 | Wilk | | 5,226,908 A | 7/1993 | Yoon |
| 4,957,498 A | 9/1990 | Caspari et al. | | 5,234,443 A | 8/1993 | Phan et al. |
| 4,957,499 A | 9/1990 | Lipatov et al. | | 5,234,445 A | 8/1993 | Walker et al. |
| 4,961,729 A | 10/1990 | Vaillancourt | | 5,236,435 A | 8/1993 | Sewell, Jr. |
| 4,966,600 A | 10/1990 | Songer et al. | | 5,237,996 A | 8/1993 | Waldman |
| 4,981,149 A | 1/1991 | Yoon et al. | | 5,242,427 A | 9/1993 | Bilweis |
| 4,983,168 A | 1/1991 | Moorehead | | 5,242,457 A | 9/1993 | Akopov et al. |
| 4,984,581 A | 1/1991 | Stice | | 5,242,459 A | 9/1993 | Buelna |
| 4,997,436 A | 3/1991 | Oberlander | | 5,243,857 A | 9/1993 | Velez |
| 4,997,439 A | 3/1991 | Chen | | 5,246,156 A | 9/1993 | Rothfuss et al. |
| 5,002,562 A | 3/1991 | Oberlander | | 5,246,443 A | 9/1993 | Mai |
| 5,002,563 A | 3/1991 | Pyka et al. | | 5,250,033 A | 10/1993 | Evans et al. |
| 5,007,921 A | 4/1991 | Brown | | 5,250,053 A | 10/1993 | Snyder |
| 5,009,643 A | 4/1991 | Reich et al. | | 5,250,054 A | 10/1993 | Li |
| 5,015,247 A | 5/1991 | Michelson | | 5,250,058 A | 10/1993 | Miller et al. |
| 5,021,059 A | 6/1991 | Kensey et al. | | 5,254,105 A | 10/1993 | Haaga |
| 5,026,390 A | 6/1991 | Brown | | 5,254,113 A | 10/1993 | Wilk |
| 5,030,226 A | 7/1991 | Green et al. | | 5,254,126 A | 10/1993 | Filipi et al. |
| 5,032,127 A | 7/1991 | Frazee et al. | | 5,258,003 A | 11/1993 | Ciaglia et al. |
| 5,037,433 A | 8/1991 | Wilk et al. | | 5,259,846 A | 11/1993 | Granger et al. |
| 5,041,129 A | 8/1991 | Hayhurst et al. | | 5,269,792 A | 12/1993 | Kovac et al. |
| 5,047,039 A | 9/1991 | Avant et al. | | 5,275,616 A | 1/1994 | Fowler |
| 5,047,047 A | 9/1991 | Yoon | | 5,279,311 A | 1/1994 | Snyder |
| 5,053,008 A | 10/1991 | Bajaj | | 5,281,236 A | 1/1994 | Bognato et al. |
| 5,059,201 A | 10/1991 | Asnis | | 5,281,237 A | 1/1994 | Gimpelson |
| 5,061,274 A | 10/1991 | Kensey | | 5,281,422 A | 1/1994 | Badylak et al. |
| 5,074,874 A | 12/1991 | Yoon et al. | | 5,282,808 A | 2/1994 | Kovac et al. |
| 5,078,721 A | 1/1992 | McKeating | | 5,282,827 A | 2/1994 | Kensey et al. |
| 5,078,731 A | 1/1992 | Hayhurst | | 5,284,485 A | 2/1994 | Kammerer et al. |
| 5,080,664 A | 1/1992 | Jain | | 5,285,945 A | 2/1994 | Brinkerhoff et al. |
| 5,092,941 A | 3/1992 | Miura | | 5,289,963 A | 3/1994 | McGarry et al. |
| 5,100,418 A | 3/1992 | Yoon et al. | | 5,290,243 A | 3/1994 | Chodorow et al. |
| 5,100,419 A | 3/1992 | Ehlers | | 5,290,284 A | 3/1994 | Adair |
| 5,100,422 A | 3/1992 | Berguer et al. | | 5,290,297 A | 3/1994 | Phillips |
| 5,100,432 A | 3/1992 | Matsutani | | 5,290,310 A | 3/1994 | Makower et al. |
| 5,108,420 A | 4/1992 | Marks | | 5,292,309 A | 3/1994 | Van Tassel et al. |
| 5,108,421 A | 4/1992 | Fowler | | 5,292,327 A | 3/1994 | Dodd et al. |
| 5,109,780 A | 5/1992 | Slouf et al. | | 5,292,332 A | 3/1994 | Lee |
| 5,114,032 A | 5/1992 | Laidlaw | | 5,293,881 A | 3/1994 | Green et al. |
| 5,114,065 A | 5/1992 | Storace | | 5,295,993 A | 3/1994 | Green |
| 5,116,349 A | 5/1992 | Aranyi | | 5,300,085 A | 4/1994 | Yock |
| 5,122,122 A | 6/1992 | Allgood | | 5,304,184 A | 4/1994 | Hathaway et al. |
| 5,122,156 A | 6/1992 | Granger et al. | | 5,304,185 A | 4/1994 | Taylor |
| 5,129,882 A | 7/1992 | Weldon et al. | | 5,304,204 A | 4/1994 | Bregen |
| 5,129,912 A | 7/1992 | Noda et al. | | 5,306,254 A | 4/1994 | Nash et al. |
| 5,129,913 A | 7/1992 | Ruppert | | 5,312,024 A | 5/1994 | Grant et al. |
| 5,131,379 A | 7/1992 | Sewell, Jr. | | 5,312,423 A | 5/1994 | Rosenbluth et al. |
| 5,144,961 A | 9/1992 | Chen et al. | | 5,318,542 A | 6/1994 | Hirsch et al. |
| 5,147,373 A | 9/1992 | Ferzli | | 5,318,578 A | 6/1994 | Hasson |
| 5,147,381 A | 9/1992 | Heimerl et al. | | 5,320,629 A | 6/1994 | Noda et al. |
| 5,156,609 A | 10/1992 | Nakao et al. | | 5,320,632 A | 6/1994 | Heidmueller |
| 5,156,788 A | 10/1992 | Chesterfield et al. | | 5,320,639 A | 6/1994 | Rudnick |
| 5,160,339 A | 11/1992 | Chen et al. | | 5,330,445 A | 7/1994 | Haaga |
| 5,163,946 A | 11/1992 | Li | | 5,330,491 A | 7/1994 | Walker et al. |
| 5,167,634 A | 12/1992 | Corrigan, Jr. et al. | | 5,334,216 A | 8/1994 | Vidal et al. |
| 5,167,643 A | 12/1992 | Lynn | | 5,334,217 A | 8/1994 | Das |
| 5,171,249 A | 12/1992 | Stefanchik et al. | | 5,335,680 A | 8/1994 | Moore |
| 5,171,250 A | 12/1992 | Yoon | | 5,336,229 A | 8/1994 | Noda |
| 5,171,251 A | 12/1992 | Bregen et al. | | 5,336,230 A | 8/1994 | Leichtling et al. |
| 5,176,648 A | 1/1993 | Holmes et al. | | 5,336,231 A | 8/1994 | Adair |
| 5,176,691 A | 1/1993 | Pierce | | 5,340,360 A | 8/1994 | Stefanchik |
| 5,178,629 A | 1/1993 | Kammerer | | 5,342,369 A | 8/1994 | Harryman, II |
| 5,192,287 A | 3/1993 | Fournier et al. | | 5,350,399 A | 9/1994 | Erlebacher et al. |
| 5,192,288 A | 3/1993 | Thompson et al. | | 5,352,229 A | 10/1994 | Goble et al. |
| 5,192,294 A | 3/1993 | Blake, III | | 5,354,279 A | 10/1994 | Hofling |
| 5,192,300 A | 3/1993 | Fowler | | 5,354,312 A | 10/1994 | Brinkerhoff et al. |
| 5,192,301 A | 3/1993 | Kamiya et al. | | 5,364,406 A | 11/1994 | Sewell, Jr. |
| 5,192,302 A | 3/1993 | Kensey et al. | | 5,364,407 A | 11/1994 | Poll |
| 5,192,602 A | 3/1993 | Spencer et al. | | 5,364,408 A | 11/1994 | Gordon |
| 5,201,744 A | 4/1993 | Jones | | 5,366,458 A | 11/1994 | Korthoff et al. |
| 5,207,703 A | 5/1993 | Jain | | 5,366,479 A | 11/1994 | McGarry et al. |

| | | | | | | |
|---|---|---|---|---|---|---|
| 5,368,595 A | 11/1994 | Lewis | | 5,522,840 A | 6/1996 | Krajicek |
| 5,368,601 A | 11/1994 | Sauer et al. | | 5,527,321 A | 6/1996 | Hinchliffe |
| 5,374,275 A | 12/1994 | Bradley et al. | | 5,527,322 A | 6/1996 | Klein et al. |
| 5,374,278 A | 12/1994 | Chesterfield et al. | | D372,310 S | 7/1996 | Hartnett |
| 5,376,096 A | 12/1994 | Foster | | 5,531,700 A | 7/1996 | Moore et al. |
| 5,383,896 A | 1/1995 | Gershony et al. | | 5,536,251 A | 7/1996 | Evard et al. |
| 5,383,905 A | 1/1995 | Golds et al. | | 5,536,267 A | 7/1996 | Edwards |
| 5,385,569 A | 1/1995 | Swor | | 5,536,273 A | 7/1996 | Lehrer |
| RE34,866 E | 2/1995 | Kensey et al. | | 5,540,701 A | 7/1996 | Sharkey et al. |
| 5,387,221 A | 2/1995 | Bisgaard | | 5,540,704 A | 7/1996 | Gordon et al. |
| 5,387,227 A | 2/1995 | Grice | | 5,540,712 A | 7/1996 | Kleshinski et al. |
| 5,391,176 A | 2/1995 | de la Torre | | 5,540,716 A | 7/1996 | Hlavacek |
| 5,391,182 A | 2/1995 | Chin | | 5,544,802 A | 8/1996 | Crainich |
| 5,392,978 A | 2/1995 | Velez et al. | | 5,545,171 A | 8/1996 | Sharkey et al. |
| 5,395,030 A | 3/1995 | Kuramoto et al. | | 5,545,178 A | 8/1996 | Kensey et al. |
| 5,395,332 A | 3/1995 | Ressemann et al. | | 5,545,180 A | 8/1996 | Le et al. |
| 5,395,349 A | 3/1995 | Quiachon et al. | | 5,547,474 A | 8/1996 | Kloeckl et al. |
| 5,397,310 A | 3/1995 | Chu et al. | | 5,549,618 A | 8/1996 | Fleenor et al. |
| 5,397,325 A | 3/1995 | Della Badia et al. | | 5,549,631 A | 8/1996 | Bonutti |
| 5,397,326 A | 3/1995 | Mangum | | 5,554,162 A | 9/1996 | DeLange |
| 5,403,329 A | 4/1995 | Hinchcliffe | | 5,560,532 A | 10/1996 | DeFonzo et al. |
| 5,403,330 A | 4/1995 | Tuason | | 5,562,684 A | 10/1996 | Kammerer |
| 5,403,331 A | 4/1995 | Chesterfield et al. | | 5,562,686 A | 10/1996 | Sauer et al. |
| 5,403,338 A | 4/1995 | Milo | | 5,562,688 A | 10/1996 | Riza |
| 5,411,481 A | 5/1995 | Allen et al. | | 5,562,728 A | 10/1996 | Lazarus et al. |
| 5,411,520 A | 5/1995 | Nash et al. | | 5,567,435 A | 10/1996 | Hubbell et al. |
| 5,413,571 A | 5/1995 | Katsaros et al. | | 5,569,269 A | 10/1996 | Hart et al. |
| 5,413,584 A | 5/1995 | Schulze | | 5,569,271 A | 10/1996 | Hoel |
| 5,416,584 A | 5/1995 | Kay | | 5,571,120 A | 11/1996 | Yoon |
| 5,417,699 A | 5/1995 | Klein et al. | | 5,573,540 A | 11/1996 | Yoon |
| 5,419,765 A | 5/1995 | Weldon et al. | | 5,573,784 A | 11/1996 | Badylak et al. |
| 5,419,777 A | 5/1995 | Hofling | | 5,575,771 A | 11/1996 | Walinsky |
| 5,423,857 A | 6/1995 | Rosenman et al. | | 5,584,842 A | 12/1996 | Fogarty et al. |
| 5,425,489 A | 6/1995 | Shichman et al. | | 5,584,879 A | 12/1996 | Reimold et al. |
| 5,425,705 A | 6/1995 | Evard et al. | | 5,591,177 A | 1/1997 | Lehrer |
| 5,425,740 A | 6/1995 | Hutchinson, Jr. | | 5,591,179 A | 1/1997 | Edelstein |
| 5,431,639 A | 7/1995 | Shaw | | 5,591,205 A | 1/1997 | Fowler |
| 5,431,666 A | 7/1995 | Sauer et al. | | 5,591,206 A | 1/1997 | Moufarrege |
| 5,431,667 A | 7/1995 | Thompson et al. | | 5,593,412 A | 1/1997 | Martinez et al. |
| 5,433,700 A | 7/1995 | Peters | | 5,593,421 A | 1/1997 | Bauer |
| 5,433,721 A | 7/1995 | Hooven et al. | | 5,601,602 A | 2/1997 | Fowler |
| 5,437,631 A | 8/1995 | Janzen | | 5,603,718 A | 2/1997 | Xu |
| 5,439,479 A | 8/1995 | Shichman et al. | | 5,607,435 A | 3/1997 | Sachdeva et al. |
| 5,443,477 A | 8/1995 | Marin et al. | | 5,609,597 A | 3/1997 | Lehrer |
| 5,443,481 A | 8/1995 | Lee | | 5,611,794 A | 3/1997 | Sauer et al. |
| 5,449,359 A | 9/1995 | Groiso | | 5,613,974 A | 3/1997 | Andreas et al. |
| 5,452,733 A | 9/1995 | Sterman et al. | | 5,613,975 A | 3/1997 | Christy |
| 5,454,822 A | 10/1995 | Schob et al. | | 5,618,291 A | 4/1997 | Thompson et al. |
| 5,454,834 A | 10/1995 | Boebel et al. | | 5,620,452 A | 4/1997 | Yoon |
| 5,456,400 A | 10/1995 | Shichman et al. | | 5,620,461 A | 4/1997 | Muijs et al. |
| 5,458,574 A | 10/1995 | Machold et al. | | 5,624,446 A | 4/1997 | Harryman, II |
| 5,462,560 A | 10/1995 | Stevens | | 5,626,588 A | 5/1997 | Sauer et al. |
| 5,462,561 A * | 10/1995 | Voda ............... 606/144 | | 5,643,289 A | 7/1997 | Sauer et al. |
| 5,464,426 A | 11/1995 | Bonutti | | 5,643,295 A | 7/1997 | Yoon |
| 5,466,241 A | 11/1995 | Leroy et al. | | 5,643,318 A | 7/1997 | Tsukernik et al. |
| 5,470,010 A | 11/1995 | Rothfuss et al. | | 5,645,565 A | 7/1997 | Rudd et al. |
| 5,470,338 A | 11/1995 | Whitfield et al. | | 5,645,566 A | 7/1997 | Brenneman et al. |
| 5,474,557 A | 12/1995 | Mai | | 5,645,567 A | 7/1997 | Crainich |
| 5,476,469 A | 12/1995 | Hathaway et al. | | 5,647,372 A | 7/1997 | Tovey et al. |
| 5,476,470 A | 12/1995 | Fitzgibbons, Jr. | | 5,649,959 A | 7/1997 | Hannam et al. |
| 5,478,309 A | 12/1995 | Sweezer et al. | | D383,539 S | 9/1997 | Croley |
| 5,478,352 A | 12/1995 | Fowler | | 5,662,664 A | 9/1997 | Gordon et al. |
| 5,478,353 A * | 12/1995 | Yoon ............... 606/213 | | 5,669,917 A | 9/1997 | Sauer et al. |
| 5,478,354 A | 12/1995 | Tovey et al. | | 5,672,174 A | 9/1997 | Gough et al. |
| 5,480,407 A | 1/1996 | Wan et al. | | 5,674,231 A | 10/1997 | Green et al. |
| 5,486,190 A | 1/1996 | Green | | 5,676,689 A | 10/1997 | Kensey et al. |
| 5,486,195 A | 1/1996 | Myers et al. | | 5,676,974 A | 10/1997 | Valdes et al. |
| 5,489,295 A | 2/1996 | Piplani et al. | | 5,681,334 A | 10/1997 | Evans et al. |
| 5,492,119 A | 2/1996 | Abrams | | 5,683,405 A | 11/1997 | Yacoubian et al. |
| 5,496,332 A | 3/1996 | Sierra et al. | | 5,690,674 A | 11/1997 | Diaz |
| 5,497,933 A | 3/1996 | DeFonzo et al. | | 5,693,061 A | 12/1997 | Pierce et al. |
| 5,507,744 A | 4/1996 | Tay et al. | | 5,695,504 A | 12/1997 | Gifford, III et al. |
| 5,507,755 A | 4/1996 | Gresl et al. | | 5,695,505 A | 12/1997 | Yoon |
| 5,507,757 A | 4/1996 | Sauer et al. | | 5,695,524 A | 12/1997 | Kelley et al. |
| 5,507,758 A | 4/1996 | Thomason et al. | | 5,700,273 A | 12/1997 | Buelna et al. |
| 5,509,902 A | 4/1996 | Raulerson | | 5,707,379 A | 1/1998 | Fleenor et al. |
| 5,520,655 A | 5/1996 | Davila et al. | | 5,713,899 A | 2/1998 | Marnay et al. |
| 5,520,665 A | 5/1996 | Fleetwood | | 5,713,910 A | 2/1998 | Gordon et al. |
| 5,520,702 A | 5/1996 | Sauer et al. | | 5,716,369 A | 2/1998 | Riza |

| Patent | Date | Name |
|---|---|---|
| 5,716,375 A | 2/1998 | Fowler |
| 5,720,574 A | 2/1998 | Barella |
| 5,720,755 A | 2/1998 | Dakov |
| 5,720,757 A | 2/1998 | Hathaway et al. |
| 5,722,981 A | 3/1998 | Stevens |
| 5,725,498 A | 3/1998 | Janzen et al. |
| 5,725,552 A | 3/1998 | Kotula et al. |
| 5,725,554 A | 3/1998 | Simon et al. |
| 5,728,109 A | 3/1998 | Schulze et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,133 A | 3/1998 | Kontos |
| 5,728,143 A | 3/1998 | Gough et al. |
| 5,728,151 A | 3/1998 | Garrison et al. |
| 5,732,872 A | 3/1998 | Bolduc et al. |
| 5,735,873 A | 4/1998 | MacLean |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,759,188 A | 6/1998 | Yoon |
| 5,759,189 A | 6/1998 | Ferragamo et al. |
| 5,766,183 A | 6/1998 | Sauer |
| 5,766,186 A | 6/1998 | Faraz et al. |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,779,707 A | 7/1998 | Bertholet et al. |
| 5,779,719 A | 7/1998 | Klein et al. |
| 5,782,844 A | 7/1998 | Yoon et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,799,661 A | 9/1998 | Boyd et al. |
| 5,810,776 A | 9/1998 | Bacich et al. |
| 5,810,846 A | 9/1998 | Virnich et al. |
| 5,810,849 A | 9/1998 | Kontos |
| 5,810,850 A | 9/1998 | Hathaway et al. |
| 5,810,851 A | 9/1998 | Yoon |
| 5,817,113 A * | 10/1998 | Gifford et al. ............... 606/153 |
| 5,820,631 A | 10/1998 | Nobles |
| 5,824,010 A | 10/1998 | McDonald |
| 5,824,111 A | 10/1998 | Schall et al. |
| 5,827,298 A | 10/1998 | Hart et al. |
| 5,830,125 A | 11/1998 | Scribner et al. |
| 5,833,698 A | 11/1998 | Hinchliffe et al. |
| 5,836,955 A | 11/1998 | Buelna et al. |
| 5,836,956 A | 11/1998 | Buelna et al. |
| 5,843,167 A | 12/1998 | Dwyer et al. |
| 5,846,253 A | 12/1998 | Buelna et al. |
| 5,848,714 A | 12/1998 | Robson et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,855,585 A | 1/1999 | Kontos |
| 5,858,082 A | 1/1999 | Cruz et al. |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,868,755 A | 2/1999 | Kanner et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,502 A | 2/1999 | Suryadevara |
| 5,871,525 A | 2/1999 | Edwards et al. |
| 5,873,876 A | 2/1999 | Christy |
| 5,876,411 A | 3/1999 | Kontos |
| 5,879,366 A | 3/1999 | Shaw et al. |
| 5,891,088 A | 4/1999 | Thompson et al. |
| 5,897,487 A | 4/1999 | Ouchi |
| 5,897,564 A | 4/1999 | Schulze et al. |
| 5,902,310 A | 5/1999 | Foerster et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A * | 7/1999 | Taheri ............................ 606/219 |
| 5,921,994 A | 7/1999 | Andreas et al. |
| 5,922,009 A | 7/1999 | Epstein et al. |
| 5,928,266 A | 7/1999 | Kontos |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,951,518 A | 9/1999 | Licata et al. |
| 5,951,547 A | 9/1999 | Gough et al. |
| 5,951,576 A | 9/1999 | Wakabayashi |
| 5,951,589 A | 9/1999 | Epstein et al. |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A * | 10/1999 | Lafontaine et al. ........... 606/213 |
| 5,972,009 A * | 10/1999 | Fortier et al. ................. 606/157 |
| 5,972,030 A | 10/1999 | Garrison et al. |
| 5,976,161 A | 11/1999 | Kirsch et al. |
| 5,980,517 A | 11/1999 | Gough et al. |
| 5,980,539 A | 11/1999 | Kontos |
| 5,984,934 A | 11/1999 | Ashby et al. |
| 5,984,949 A | 11/1999 | Levin |
| 5,984,950 A * | 11/1999 | Cragg et al. .................. 606/216 |
| 5,993,466 A | 11/1999 | Yoon |
| 5,993,468 A | 11/1999 | Rygaard |
| 5,993,476 A | 11/1999 | Groiso |
| 5,997,555 A | 12/1999 | Kontos |
| 6,001,109 A | 12/1999 | Kontos |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,022,372 A | 2/2000 | Kontos |
| 6,024,747 A | 2/2000 | Kontos |
| 6,024,750 A | 2/2000 | Mastri et al. |
| 6,030,364 A | 2/2000 | Durgin et al. |
| 6,030,413 A | 2/2000 | Lazarus |
| 6,033,427 A | 3/2000 | Lee |
| 6,036,699 A | 3/2000 | Andreas et al. |
| 6,036,703 A | 3/2000 | Evans et al. |
| 6,036,720 A | 3/2000 | Abrams et al. |
| 6,042,601 A | 3/2000 | Smith |
| 6,045,570 A | 4/2000 | Epstein et al. |
| 6,048,351 A | 4/2000 | Gordon et al. |
| 6,048,354 A | 4/2000 | Lawrence |
| 6,048,357 A | 4/2000 | Kontos |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |

| | | | |
|---|---|---|---|
| 6,068,603 A | 5/2000 | Suzuki | |
| 6,071,300 A | 6/2000 | Brenneman et al. | |
| 6,077,276 A | 6/2000 | Kontos | |
| 6,077,279 A | 6/2000 | Kontos | |
| 6,077,281 A | 6/2000 | Das | |
| 6,077,291 A | 6/2000 | Das | |
| 6,080,182 A | 6/2000 | Shaw et al. | |
| 6,080,183 A | 6/2000 | Tsugita et al. | |
| 6,083,242 A | 7/2000 | Cook | |
| 6,090,130 A | 7/2000 | Nash et al. | |
| 6,102,271 A | 8/2000 | Longo et al. | |
| 6,110,184 A | 8/2000 | Weadock | |
| 6,113,612 A | 9/2000 | Swanson et al. | |
| 6,117,125 A | 9/2000 | Rothbarth et al. | |
| 6,117,144 A | 9/2000 | Nobles et al. | |
| 6,117,145 A | 9/2000 | Wood et al. | |
| 6,117,148 A | 9/2000 | Ravo | |
| 6,117,157 A | 9/2000 | Tekulve | |
| 6,120,524 A * | 9/2000 | Taheri | 606/213 |
| 6,126,675 A | 10/2000 | Shchervinsky et al. | |
| 6,132,439 A | 10/2000 | Kontos | |
| 6,132,440 A | 10/2000 | Hathaway et al. | |
| 6,136,010 A | 10/2000 | Modesitt et al. | |
| 6,139,556 A | 10/2000 | Kontos | |
| 6,143,004 A | 11/2000 | Davis | |
| 6,149,660 A | 11/2000 | Laufer et al. | |
| 6,149,667 A | 11/2000 | Hovland et al. | |
| 6,152,144 A | 11/2000 | Lesh et al. | |
| 6,152,936 A | 11/2000 | Christy et al. | |
| 6,152,937 A | 11/2000 | Peterson et al. | |
| 6,165,204 A | 12/2000 | Levinson et al. | |
| 6,171,277 B1 | 1/2001 | Ponzi | |
| 6,171,329 B1 | 1/2001 | Shaw et al. | |
| 6,190,396 B1 | 2/2001 | Whitin et al. | |
| 6,193,708 B1 | 2/2001 | Ken et al. | |
| 6,193,734 B1 | 2/2001 | Bolduc et al. | |
| 6,197,042 B1 | 3/2001 | Ginn et al. | |
| 6,198,974 B1 | 3/2001 | Webster, Jr. | |
| 6,200,329 B1 | 3/2001 | Fung et al. | |
| 6,206,893 B1 | 3/2001 | Klein et al. | |
| 6,206,913 B1 | 3/2001 | Yencho et al. | |
| 6,206,931 B1 | 3/2001 | Cook et al. | |
| 6,210,407 B1 | 4/2001 | Webster | |
| 6,220,248 B1 | 4/2001 | Voegele et al. | |
| 6,221,084 B1 | 4/2001 | Fleenor | |
| 6,221,102 B1 | 4/2001 | Baker et al. | |
| 6,245,079 B1 | 6/2001 | Nobles et al. | |
| 6,248,124 B1 | 6/2001 | Pedros et al. | |
| 6,254,617 B1 | 7/2001 | Spence et al. | |
| 6,254,642 B1 | 7/2001 | Taylor | |
| 6,276,704 B1 | 8/2001 | Suiter | |
| 6,277,140 B2 | 8/2001 | Ginn et al. | |
| 6,280,460 B1 | 8/2001 | Bolduc et al. | |
| 6,287,322 B1 | 9/2001 | Zhu et al. | |
| 6,296,657 B1 | 10/2001 | Brucker | |
| 6,305,891 B1 | 10/2001 | Burlingame | |
| 6,306,081 B1 | 10/2001 | Ishikawa et al. | |
| 6,319,258 B1 | 11/2001 | McAllen, III et al. | |
| 6,322,580 B1 | 11/2001 | Kanner | |
| 6,328,727 B1 | 12/2001 | Frazier et al. | |
| 6,329,386 B1 | 12/2001 | Mollison | |
| 6,334,865 B1 | 1/2002 | Redmond et al. | |
| 6,348,059 B1 | 2/2002 | Hathaway et al. | |
| 6,348,064 B1 | 2/2002 | Kanner | |
| 6,355,050 B1 | 3/2002 | Andreas et al. | |
| 6,358,258 B1 | 3/2002 | Arcia et al. | |
| 6,375,671 B1 | 4/2002 | Kobayashi et al. | |
| D457,958 S | 5/2002 | Dycus | |
| 6,383,208 B1 | 5/2002 | Sancoff et al. | |
| 6,391,048 B1 | 5/2002 | Ginn et al. | |
| 6,395,015 B1 | 5/2002 | Borst et al. | |
| 6,397,110 B1 | 5/2002 | Kuzma | |
| 6,398,752 B1 | 6/2002 | Sweezer et al. | |
| 6,402,765 B1 | 6/2002 | Monassevitch et al. | |
| 6,409,739 B1 | 6/2002 | Nobles et al. | |
| 6,419,669 B1 | 7/2002 | Frazier et al. | |
| 6,423,054 B1 | 7/2002 | Ouchi | |
| 6,425,911 B1 | 7/2002 | Akerfeldt et al. | |
| 6,428,472 B1 | 8/2002 | Haas | |
| 6,428,548 B1 | 8/2002 | Durgin et al. | |
| 6,428,549 B1 | 8/2002 | Kontos | |
| 6,436,109 B1 | 8/2002 | Kontos | |
| 6,443,158 B1 | 9/2002 | Lafontaine et al. | |
| 6,443,963 B1 | 9/2002 | Baldwin et al. | |
| 6,447,540 B1 | 9/2002 | Fontaine et al. | |
| 6,450,391 B1 | 9/2002 | Kayan et al. | |
| 6,451,031 B1 | 9/2002 | Kontos | |
| 6,458,130 B1 | 10/2002 | Frazier et al. | |
| 6,461,364 B1 | 10/2002 | Ginn et al. | |
| 6,461,366 B1 | 10/2002 | Seguin | |
| 6,482,224 B1 * | 11/2002 | Michler et al. | 606/219 |
| 6,488,692 B1 | 12/2002 | Spence et al. | |
| 6,500,115 B2 | 12/2002 | Krattiger et al. | |
| 6,506,210 B1 | 1/2003 | Kanner | |
| 6,508,828 B1 | 1/2003 | Akerfeldt et al. | |
| 6,511,489 B2 | 1/2003 | Field et al. | |
| 6,517,498 B1 | 2/2003 | Burbank et al. | |
| 6,517,553 B2 | 2/2003 | Klein et al. | |
| 6,517,569 B2 | 2/2003 | Mikus et al. | |
| 6,533,762 B2 | 3/2003 | Kanner et al. | |
| 6,533,812 B2 | 3/2003 | Swanson et al. | |
| 6,537,288 B2 | 3/2003 | Vargas et al. | |
| 6,547,806 B1 | 4/2003 | Ding | |
| 6,551,319 B2 | 4/2003 | Lieberman | |
| 6,551,330 B1 | 4/2003 | Bain et al. | |
| 6,558,399 B1 | 5/2003 | Isbell et al. | |
| 6,562,052 B2 | 5/2003 | Nobles et al. | |
| 6,569,159 B1 | 5/2003 | Edwards et al. | |
| 6,569,173 B1 | 5/2003 | Blatter et al. | |
| 6,569,185 B2 | 5/2003 | Ungs | |
| 6,572,629 B2 | 6/2003 | Kalloo et al. | |
| 6,582,452 B2 | 6/2003 | Coleman et al. | |
| 6,582,482 B2 | 6/2003 | Gillman et al. | |
| 6,596,012 B2 | 7/2003 | Akerfeldt et al. | |
| 6,599,303 B1 | 7/2003 | Peterson et al. | |
| 6,602,263 B1 | 8/2003 | Swanson et al. | |
| 6,610,072 B1 | 8/2003 | Christy et al. | |
| 6,613,059 B2 | 9/2003 | Schaller et al. | |
| 6,613,060 B2 * | 9/2003 | Adams et al. | 606/157 |
| 6,616,686 B2 | 9/2003 | Coleman et al. | |
| 6,623,509 B2 | 9/2003 | Ginn | |
| 6,623,510 B2 | 9/2003 | Carley et al. | |
| 6,626,918 B1 | 9/2003 | Ginn et al. | |
| 6,632,237 B2 | 10/2003 | Ben-David et al. | |
| 6,632,238 B2 | 10/2003 | Ginn et al. | |
| 6,634,537 B2 | 10/2003 | Chen | |
| 6,641,592 B1 | 11/2003 | Sauer et al. | |
| 6,645,205 B2 | 11/2003 | Ginn | |
| 6,652,538 B2 | 11/2003 | Kayan et al. | |
| 6,652,556 B1 | 11/2003 | VanTassel et al. | |
| 6,663,655 B2 | 12/2003 | Ginn et al. | |
| 6,669,714 B2 | 12/2003 | Coleman et al. | |
| 6,676,671 B2 | 1/2004 | Robertson et al. | |
| 6,676,685 B2 * | 1/2004 | Pedros et al. | 606/213 |
| 6,679,904 B2 * | 1/2004 | Gleeson et al. | 606/219 |
| 6,689,051 B2 | 2/2004 | Nakada et al. | |
| 6,689,147 B1 | 2/2004 | Koster, Jr. | |
| 6,695,867 B2 | 2/2004 | Ginn et al. | |
| 6,699,256 B1 | 3/2004 | Logan et al. | |
| 6,702,826 B2 | 3/2004 | Liddicoat et al. | |
| 6,712,836 B1 | 3/2004 | Berg et al. | |
| 6,712,837 B2 | 3/2004 | Akerfeldt et al. | |
| 6,716,228 B2 | 4/2004 | Tal | |
| 6,719,777 B2 | 4/2004 | Ginn et al. | |
| 6,726,704 B1 | 4/2004 | Loshakove et al. | |
| 6,743,195 B2 | 6/2004 | Zucker | |
| 6,743,243 B1 | 6/2004 | Roy et al. | |
| 6,743,259 B2 | 6/2004 | Ginn | |
| 6,745,079 B2 | 6/2004 | King | |
| 6,746,457 B2 | 6/2004 | Dana et al. | |
| 6,749,621 B2 | 6/2004 | Pantages et al. | |
| 6,749,622 B2 | 6/2004 | McGuckin et al. | |
| 6,755,842 B2 | 6/2004 | Kanner et al. | |
| 6,767,356 B2 | 7/2004 | Kanner et al. | |
| 6,776,785 B1 | 8/2004 | Yencho et al. | |
| 6,780,197 B2 | 8/2004 | Roe et al. | |
| 6,786,915 B2 | 9/2004 | Akerfeldt et al. | |
| 6,790,218 B2 | 9/2004 | Jayaraman | |

| | | |
|---|---|---|
| 6,790,220 B2 | 9/2004 | Morris et al. |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,911,034 B2 | 6/2005 | Nobles et al. |
| 6,926,723 B1 | 8/2005 | Mulhauser et al. |
| 6,926,731 B2 | 8/2005 | Coleman et al. |
| 6,939,357 B2 | 9/2005 | Navarro et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,029,480 B2 | 4/2006 | Klein et al. |
| 7,029,481 B1 | 4/2006 | Burdulis, Jr. et al. |
| 7,033,379 B2 | 4/2006 | Peterson |
| 7,048,747 B2 | 5/2006 | Arcia et al. |
| 7,060,084 B1 * | 6/2006 | Loshakove et al. ............ 606/213 |
| 7,063,661 B2 | 6/2006 | Okada |
| 7,063,710 B2 | 6/2006 | Takamoto et al. |
| 7,063,711 B1 * | 6/2006 | Loshakove et al. ............ 606/153 |
| 7,083,635 B2 | 8/2006 | Ginn |
| 7,108,709 B2 | 9/2006 | Cummins |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |
| 7,160,309 B2 | 1/2007 | Voss |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,179,266 B2 | 2/2007 | Kontos |
| 7,211,101 B2 | 5/2007 | Carley et al. |
| 7,229,458 B2 | 6/2007 | Boecker et al. |
| 7,235,087 B2 | 6/2007 | Modesitt et al. |
| 7,270,672 B1 | 9/2007 | Singer |
| 7,311,720 B2 | 12/2007 | Mueller et al. |
| 7,316,704 B2 | 1/2008 | Bagaoisan et al. |
| 7,326,230 B2 * | 2/2008 | Ravikumar ............ 606/213 |
| 7,331,979 B2 | 2/2008 | Khosravi et al. |
| 7,335,220 B2 | 2/2008 | Khosravi et al. |
| 7,338,514 B2 * | 3/2008 | Wahr et al. ............ 606/213 |
| D566,272 S | 4/2008 | Walburg et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,396,359 B1 * | 7/2008 | Derowe et al. ............ 606/213 |
| 7,431,727 B2 | 10/2008 | Cole et al. |
| 7,445,626 B2 | 11/2008 | Songer et al. |
| 7,449,024 B2 | 11/2008 | Stafford |
| 7,462,188 B2 | 12/2008 | McIntosh |
| 7,507,200 B2 | 3/2009 | Okada |
| 7,533,790 B1 | 5/2009 | Knodel et al. |
| 7,597,706 B2 | 10/2009 | Kanner et al. |
| 7,648,493 B2 * | 1/2010 | Forsberg et al. ............ 604/523 |
| D611,144 S | 3/2010 | Reynolds |
| 7,727,249 B2 | 6/2010 | Rahmani |
| 7,731,655 B2 | 6/2010 | Smith et al. |
| 7,749,249 B2 * | 7/2010 | Gelbart et al. ............ 606/216 |
| 7,806,904 B2 | 10/2010 | Carley et al. |
| 7,819,895 B2 | 10/2010 | Ginn et al. |
| 7,901,428 B2 * | 3/2011 | Ginn et al. ............ 606/213 |
| 2001/0046518 A1 | 11/2001 | Sawhney |
| 2001/0053909 A1 | 12/2001 | Nakada |
| 2002/0099389 A1 | 7/2002 | Michler et al. |
| 2002/0106409 A1 | 8/2002 | Sawhney et al. |
| 2002/0188275 A1 | 12/2002 | McGuckin et al. |
| 2003/0233095 A1 * | 12/2003 | Urbanski et al. ............ 606/72 |
| 2004/0009205 A1 | 1/2004 | Sawhney |
| 2004/0093027 A1 | 5/2004 | Fabisiak et al. |
| 2004/0098044 A1 * | 5/2004 | Van de Moer et al. ....... 606/213 |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0267193 A1 | 12/2004 | Bagaoisan et al. |
| 2004/0267308 A1 | 12/2004 | Bagaoisan et al. |
| 2005/0010248 A1 * | 1/2005 | Lafontaine ............ 606/213 |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0234396 A1 * | 10/2005 | Forsberg et al. ............ 604/43 |
| 2005/0245876 A1 | 11/2005 | Khosravi et al. |
| 2005/0256532 A1 * | 11/2005 | Nayak et al. ............ 606/151 |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0106420 A1 * | 5/2006 | Dolan et al. ............ 606/213 |
| 2006/0253037 A1 | 11/2006 | Ginn et al. |
| 2006/0253072 A1 | 11/2006 | Pai et al. |
| 2006/0259049 A1 * | 11/2006 | Harada et al. ............ 606/151 |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0083231 A1 * | 4/2007 | Lee ............ 606/213 |
| 2007/0123817 A1 | 5/2007 | Khosravi et al. |
| 2007/0198058 A1 * | 8/2007 | Gelbart et al. ............ 606/213 |
| 2007/0203506 A1 | 8/2007 | Sibbitt, Jr. et al. |
| 2008/0009794 A1 | 1/2008 | Bagaoisan et al. |
| 2008/0045979 A1 | 2/2008 | Ma |
| 2008/0065151 A1 | 3/2008 | Ginn |
| 2008/0065152 A1 | 3/2008 | Carley |
| 2008/0287967 A1 | 11/2008 | Andreas et al. |
| 2009/0088794 A1 * | 4/2009 | LaFontaine ............ 606/213 |
| 2010/0130965 A1 | 5/2010 | Sibbitt, Jr. et al. |
| 2010/0234884 A1 * | 9/2010 | Lafontaine et al. ............ 606/213 |

FOREIGN PATENT DOCUMENTS

| | | |
|---|---|---|
| WO | WO 02/062234 | 8/2002 |
| WO | WO 03/094748 | 11/2003 |
| WO | WO 2005/000126 | 1/2005 |
| WO | WO 2005/041782 | 5/2005 |
| WO | WO 2005/063129 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

U.S. Appl. No. 60/696,069, filed Jul. 1, 2005, Pantages et al.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.

U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt, Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
US 5,824,010, 6/1974, Semm, (withdrawn).
U.S. Appl. No. 11/316,775, Apr. 16, 2008, Office Action.
U.S. Appl. No. 11/316,775, Aug. 6, 2008, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,662, Oct. 26, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/508,715, Oct. 18, 2010, Office Action.
U.S. Appl. No. 12/365,397, Sep. 13, 2010, Office Action.

* cited by examiner

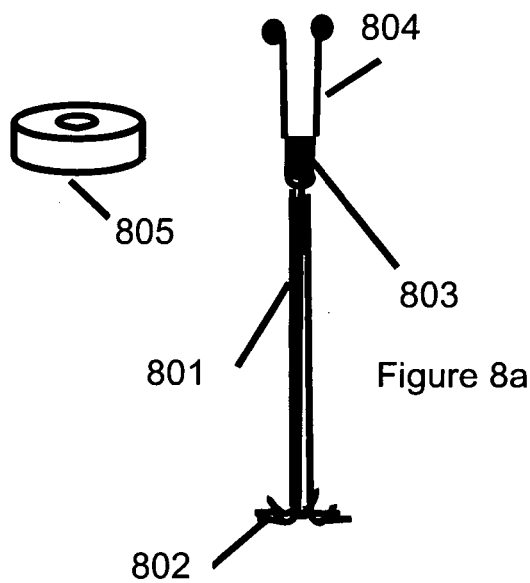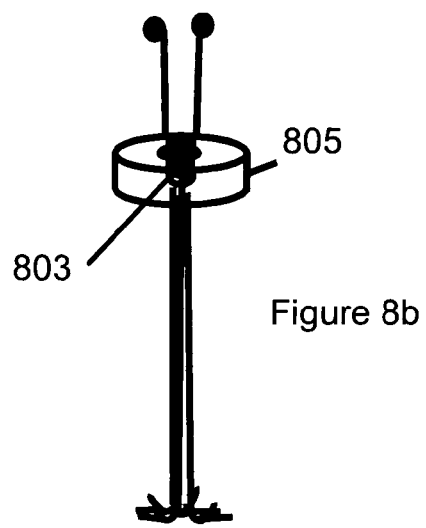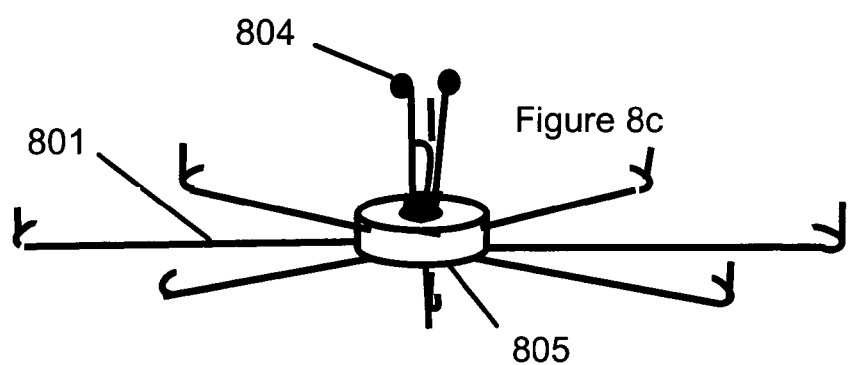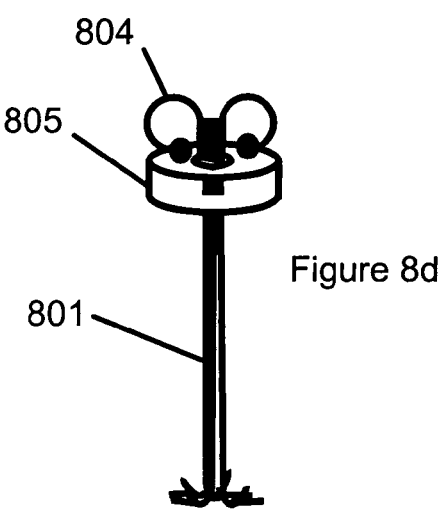

VASCULAR CLOSURE METHODS AND APPARATUSES

This application is a continuation of U.S. patent application Ser. No. 11/316,775 filed on Dec. 23, 2005, now abandoned, which is incorporated herein by reference, and which claims benefit of and priority to U.S. Provisional Patent Application No. 60/711,279, filed on Aug. 24, 2005.

BACKGROUND

The present invention relates to methods and apparatuses for closing punctures and apertures in human and animal tissue and to methods and apparatuses for inserting such an apparatus into such tissue to perform such closure functions.

During angiography and related procedures, catheters are inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, plaque removal, and infusion of a therapeutic substance. After the procedure is completed and the catheter is removed from the patient, the access hole must be closed to prevent massive hemorrhage. This is conventionally achieved by applying pressure over the blood vessel manually and then by applying a pressure bandage, compressive weight, or clamp device. With conventional methods, the rate of post-puncture hemorrhage is high, which causes considerable complications. This complication is exacerbated by the concomitant use of anticoagulant medications such as heparin or warfarin and by antiplatelet drugs, which are commonly used to treat vascular disease.

Sutures have been used to close access puncture wounds in blood vessels. U.S. Pat. No. 05,613,974 describes a device and method for applying sutures to a vascular puncture. US2004/0093027A1 describes barbed suture-like material that apposes the puncture site. US 2005/0121042 A1 describes a device and method for applying suture to a vascular puncture. Difficulties with these methods include the large number of steps necessary to deploy the needles, capture the suture, withdraw the suture, tie the knot, and cut the suture. In addition, the hole in the blood vessel is often widened by insertion of the instrument, and the suture remains intravascularly on the endothelial surface, and thus can be a nidus for thrombus or intravascular mural hyperplasia with later spontaneous and catastrophic closure of the vessel.

Extravascular plugs have also been proposed for closure of vascular punctures. U.S. Pat. Nos. 05,254,105 and 05,330,445 describe an extravascular plug which is slid down the external surface of the catheter or introducer and is placed into the puncture site in this manner. U.S. Pat. No. 05,643,318 relates to a similar device that has its own vessel locator device. US22022822A1 and US2004/0158287A1 describe an extravascular plug that is delivered with a specialized system. US24215232A1 describes an extravascular plug with an intravascular anchor set with a sheath with a detection port. US2005/0085855A1 describes an extravascular collagen plug, held in place with an intravascular anchor, and a device that locks over a piece of suture.

U.S. Pat. No. 05,906,631 describes a plug made of hydrophilic material. U.S. Pat. No. 06,126,675 describes an intravascular anchor and a bioabsorble extravascular plug. U.S. Pat. No. 06,623,509 describes a bioabsorbable plug. U.S. Pat. Nos. 06,296,657 and 06,743,195 describe an inflatable balloon that puts pressure on the puncture site. U.S. Pat. No. 06,569,185 describes an injectable vascular plug. U.S. Pat. No. 06,663,655 describes a plug that screws in the puncture tract. US2004/0143290 A1 describes a combination of an intraluminal balloon and injectable sealant. Disadvantages to these methods are related to the high likelihood of thrombosis associated with the intravascular plug or anchor, and the presence of collagen or other bioabsorble materials which cause inflammation, activate the clotting cascade, and increase the likelihood of thrombosis, which, in an arterial system, is catastrophic.

Vascular patches have also been used for repairing blood vessels, but usually only for large areas of damage. U.S. Pat. No. 05,100,422 describes a vascular patch that is sutured to the external surface of the damaged blood vessel. U.S. Pat. No. 05,100,422 describes a vascular patch achieved by instilled adhesives and the device for doing such. These are generally impractical for catheter-based methods. U.S. Pat. Nos. 06,248,124 and 05,507,744 describe devices and methods that use electrocautery for sealing vascular punctures. This also requires a complicated device, and perforation and thrombosis are very real possibilities.

Vascular clips or staples delivered through a catheter device have also been proposed. These devices have penetrating members that bring the edges of the tissue together. U.S. Pat. No. 06,695,867 describes a clip or staple that is delivered by a specialized device. U.S. Pat. No. 0,674,9622 describes a number of different clips with sharpened barbs or ends that include both intra- and extravascular portions, made of metal with memory characteristics. U.S. Pat. No. 05,861,005 describes an arterial staple that is delivered with a specialized device. U.S. Pat. No. 05,919,207 describes a stapling system based on long hooked wires that appose the surfaces, with a small staple gun to close the lesion. U.S. Pat. No. 06,022,372 describes a similar staple gun. U.S. Pat. Nos. 06,296,657, 06,663,655, and 06,749,621 describe a clip that is external to the vessel, but clips the two sides of the puncture together, and a device for achieving such. U.S. Pat. No. 5,782,861 and 5,964,782 describe clip devices composed of two or more prongs or hooks that, depending on the direction of the prongs, can clip together the puncture site from the intra- or extravascular position, through the use of a collar which forces the prongs together or other mechanisms. These clip devices are composed of thick semi-rigid material, and can be placed only with a specialized instruments, and because of the rigidity have great potential to injure or cut the blood vessel. Disadvantages of these clip devices in general include difficulty in retrieving the device if misplaced, excessive manipulation required, the thickness of the clip material which tends to cut or shear the blood vessel, the large forces that must be used to curve the staples and fix the clips, the increased possibility of tearing the blood vessel, and the general lack of control of the forces being applied to the blood vessel.

Accordingly, there is a need for methods and apparatuses that are suitable for closure of vascular punctures or other openings, and that do not suffer from the drawbacks of conventional approaches.

SUMMARY OF THE INVENTION

The present invention provides methods and apparatuses that are suitable for closure of vascular punctures or other openings, and that do not suffer from the drawbacks of conventional approaches.

The present invention comprises a tissue closure device, comprising a plurality of tissue engagement elements, mounted with each other such that in a first compressed configuration the tissue engagement elements can pass through a tissue opening to be closed, and such that in a second compressed configuration the tissue engagement elements bring the edges of the opening into apposition, and such that in an expanded configuration the tissue engagement elements span the opening, wherein the tissue engagement elements engage the tissue in the compressed configuration and in the expanded configuration.

The present invention also comprises methods for closing tissue openings, comprising passing a device while in the first compressed condition through a sheath that penetrates the proximal surface of the tissue; expelling the device from the sheath into space beyond the proximal surface of the tissue such that the device assumes the expanded configuration; c) manipulating the device such that the tissue engagement elements engage the tissue; d) causing the device to assume the second compressed configuration, bringing the edges of the opening into apposition.

The present invention can provide a catheter-delivered umbrella-like device comprising fine, strong, flexible material that after delivery expands in a blood vessel so that the individual members extend beyond the catheter edges and/or puncture dimensions. The device can be viewed as analagous in structure and design as contemporary expandable vascular filters and closure umbrellas, although its purpose and function is completely different. As the catheter is withdrawn, the device is pulled against the interior of the blood vessel and the hooks or grasping devices on the ends of the members seize the interior of the vessel wall. Because of the very fine and flexible nature of the members and their multiplicity, there is minimal shear force applied to the blood vessel. While pulling on the retaining suture to keep the device against the blood vessel, a retaining lock is then advanced distally starting at the proximal portion of the members, which causes the members to first angle the device into a conical shape and then force the individual members together in a linear parallel direction, which because the members are engaged with the vessel wall, brings the edges of the punctured tissue together into apposition. The retainer lock is then locked onto the parallel members and can keep tension on the wound externally, and can prevent intravascular migration of the device. If there is no blood leakage through the closure and the device is properly positioned and stable, then the guidewire can be removed and the retaining suture or string loop cut, resulting is complete and rapid closure, which can then heal.

Since this device brings the puncture edges together, there is true blood vessel healing with little endothelial disruption, reducing the chances of thrombosis or intimal hyperplasia. The device can be supplied in different diameters (e.g., french) to accommodate different sizes of catheters and different sizes of puncture holes.

The present invention can comprise a device with umbrella-like structure, which can be viewed as analogous to the various designs of intravascular filters and aperture seals, which are delivered in a folded or compressed form, and then expanded to their filter shapes. U.S. Pat. No. 4,969,891 describes a self-expanding removable filter device that is placed with a sheath. U.S. Pat. No. 5,634,942 and 5,634,942 describe a similar device but with two sets of arms which protrude in opposite directions. U.S. Pat. No. 6,241,746 B1 is a similar version that can be converted to a vascular stent. U.S. Pat. No. 6,361,546 is a version with a central guidewire lumen. U.S. Pat. No. 6,428,559 describes a variable-diameter vascular filter system. U.S. Pat. No. 6,485,501 B1 also describes a filter with a guidewire. US 2003/0208227 describes different construction configurations of a filter. US 2004/0087999 A1 reveals various types of structures to retain the filter in the vessel. U.S. Pat. No. 5,709,707 describes a typical umbrella-type closure device used to close apertures.

Each of the preceding patents and applications are incorporated herein by reference. The present device, analogous to many of the vascular filters and umbrella closure devices noted above, is both expandable like an umbrella and retrievable if it had to be retrieved because of misplacement. Unlike previous umbrella closure devices, the present device engages the tissue in both the expanded and compressed configurations, and functions by bringing tissue edges into apposition rather than by providing a patch that covers the opening. In addition, although the embodiments shown here generally have linear members, these members, like the structure of the intravascular filters and umbrella-type devices, need not be strictly linear, but can assume a number of complex geometrical shapes and structural patterns.

The present device, like some contemporary vascular filters, can utilize an expanding material, preferably with memory characteristics, that opens up spontaneously within the blood vessel. The device also, like some contemporary filters, can have tissue hooks or penetrators, in order to seize the vessel wall and stabilize the device. However, unlike an umbrella-style vascular filter, the device uses this opening-dosing quality to seize the edges of the puncture site, and close them, resulting in a complete vascular closure. Although the device can be viewed as analogous to some contemporary self-expanding and retractable vascular filters, it is unlike them in that in certain embodiments it has a retaining lock to force the umbrella to reassume its folded state.

DESCRIPTION OF THE FIGURES

The invention is explained by using embodiment examples and corresponding drawings, which are incorporated into and form part of the specification.

FIG. 8(a,b,c,d) is a schematic depiction of a double-action vascular closure apposition device according to the present invention.

DETAILED DESCRIPTION

The present invention provides apparatuses and methods for closing a vascular puncture wound or any tissue aperture, for example those resulting from the insertion of a vascular catheter or surgical instrument, trauma or disease. The present invention embraces both apparatus and method aspects of devices for closing a vascular puncture, and the methods for delivering such a device. The present device can be closed in the delivery system (catheter or sheath) and when discharged, be open in the blood vessel. In some embodiments, at least a portion of the device can be formed of a memory metal or similar material, as is currently done in vascular filters. The stress free state corresponds to the state at which the apparatus has opened in a blood vessel, and the stressed state in the catheter and when a retaining lock is put into position. Example embodiments of tissue closure apposition devices according to the present invention are shown in FIGS. 1, 2, 3, 4, 5, 6, and 8. The descriptions refer to "vessels" for convenience; the present invention is applicable to facilitate closure of various types of tissue openings.

Figure 1A:
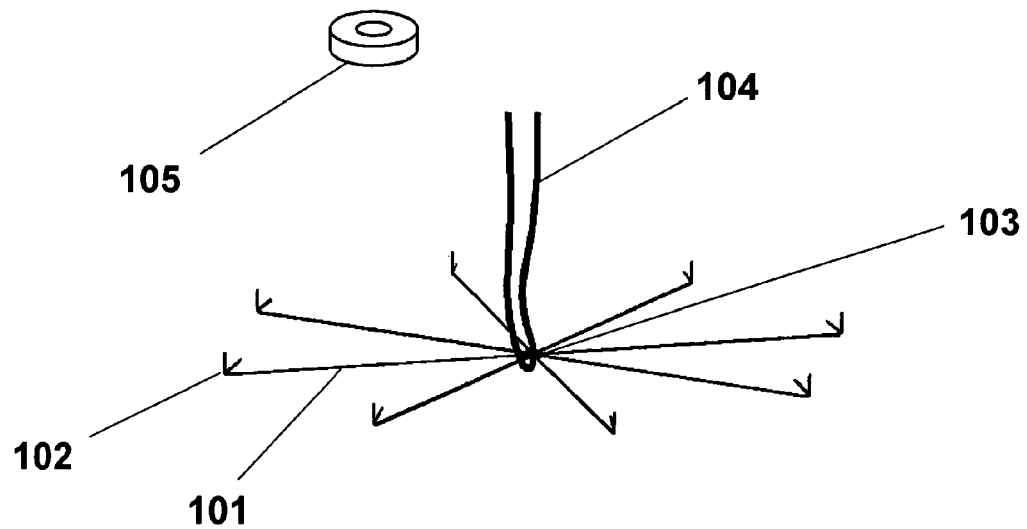
FIG. 1(a,b) is a schematic depiction of a vascular closure apposition device according to the present invention.
Figure 1B:
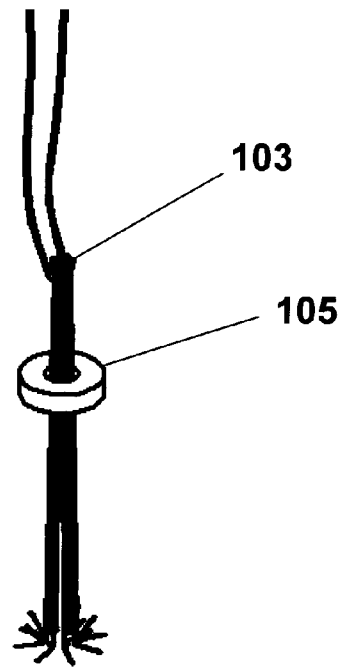

FIG. 1 (*a,b*) is a lateral view of a vascular closure apposition umbrella. A plurality of members 101 are disposed substantially radially about a central junction 103. Each of the members 101 comprise a tissue hook 102, in the figure a double hook. The central junction 103 is adapted to engage a closed loop of string or suture 104. The hooks 102 engage the tissue, and are brought and maintained together by operation of a retaining lock 105. In FIG. 1*b,* the device is shown in a closed position, where the central junction 103 has passed through the retaining lock 105.

The vascular closure apposition umbrella of FIG. 1(*a,b*) comprises 2 or more members 101 placed in apposition to each other, shown in the figure as disposed substantially radially. The members 101 in the figure are shown as straight wires, but can be curved or have a wave structure or other design, for example a design to engage a retaining lock. The members are flexible for manipulation in tissue and delivery, yet rigid enough when extended to push the tissue engagement structures against the vessel wall. The tissue engagement structures 102 in this example comprise double hooks, allowing engagement of the tissue in 102 different directions simultaneously. The tissue engagement structures can also comprise multiple hooks, a single hook, or straight engaging devices. The tissue engagement structures can be sharp in order to penetrate in one direction, but not to cut, thus, would generally not have a cutting surface other than the point. The members join in a central junction 103 which can be continuous with each of the members or can be joined to the members by any suitable method. The central junction 103 comprises an eyelet or recovery loop in which initially a closed loop of string or suture 104 engages. The eyelet or recovery loop can be used to recover the device into a catheter in the event of misplacement. A retaining lock 105 can encourage closure of the device, and can also prevent unintended intravascular migration of the device. The retaining lock 105 is shown in the figure as a washer-like device, but can take a number of different shapes and can comprise a number of different materials. For example, the retaining lock 105 can comprise plastic; metal, or composite.

In operation, the tissue closure apposition umbrella is closed within the catheter or sheath, corresponding to the illustration of FIG. 1(*b*). Once placed within the blood vessel, the umbrella can be opened within the blood vessel, corresponding to the illustration of FIG. 1(*a*), so that the hooks on the members engage the vessel wall. The umbrella can then be closed with the retaining lock. As the umbrella closes with the retaining lock, the hooks hold the edges of the puncture wound and, as they align with each other, bring the puncture wound edges in apposition. Undulations or excrescences on the members or central junction can engage corresponding locking surfaces on the retaining lock. More specific locking devices such as angled dentates, peg and hole, and male-female locking surfaces can also be suitable. A guidewire can go between the members in this particular embodiment without a specific lumen for the guidewire.

Figure 2A:
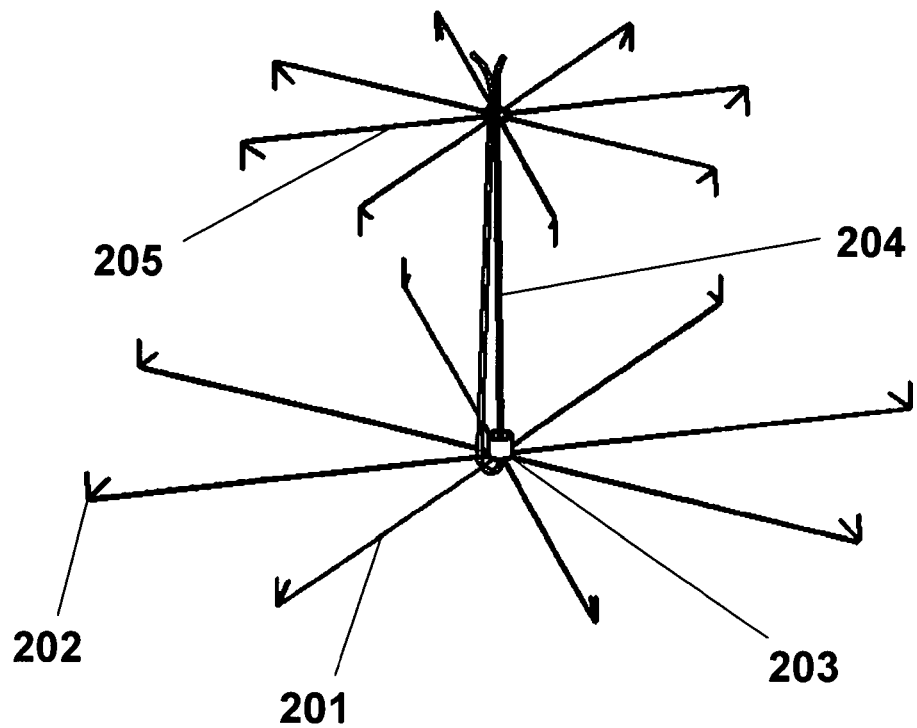
FIG. 2(a,b) is a schematic depiction of a vascular closure apposition device according to the present invention.
Figure 2B:
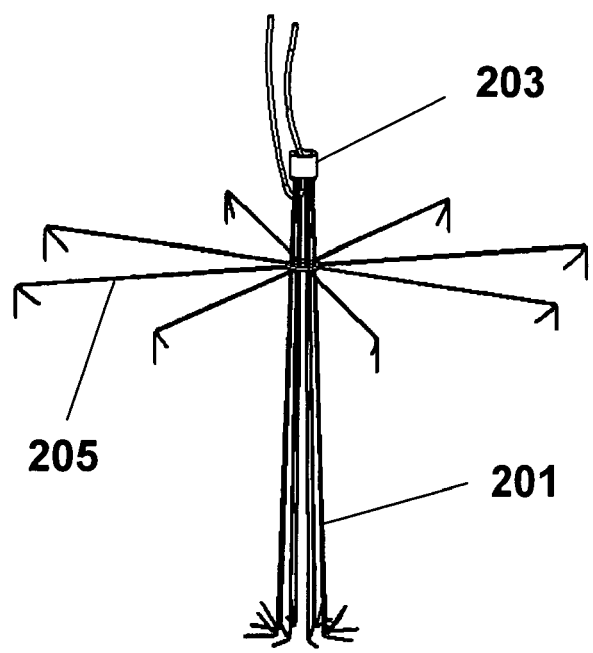

FIG. 2(*a,b*) is a lateral view of a vascular closure apposition double umbrella. A plurality of members 201 are disposed substantially radially about a central junction 203. Each member comprises a tissue engagement structure 202, shown in the figure as a hook on the end of the member. The central junction can comprise a structure compatible with a string or suture 204 to facilitate deployment and removal. A retaining lock 205, in the figure an umbrella oriented opposite the umbrella formed by members 201, closes the device. FIG. 2(*b*) shows the device with the umbrella formed by members 201 closed, bringing tissue sides in apposition, and the retaining lock 205 open, maintaining the closed position of the umbrella and providing tissue stability on the opposite side of the vessel wall.

The radial members 201 in FIG. 2(*a,b*) are shown as straight, but can have dentates or other devices compatible with engagement of the retaining lock. The string or suture 204 can be engaged with the central junction 203 to urge the central junction 203 through the retaining lock 205, encouraging the members 201 into apposition. The retaining lock of the device of FIG. 2(*a,b*) comprises another expanding umbrella, but facing the opposite direction. In the figure, the retaining lock umbrella has straight members with hooks on the ends. The retaining lock umbrella can also comprise a variety of configurations, including bent or curved members, members with various hooks or no hooks, web-like structures, and film-like members. This retaining lock comprise more complicated structure members, as examples like many constructions of intravascular stents and filters. The members 201 close and bring the tissue together as in FIG. 2(*b*); the retaining lock can provide for tissue stability in the extravascular tissues. A guidewire in this embodiment can go between the members without a specific lumen for the guidewire.

Figure 3A:
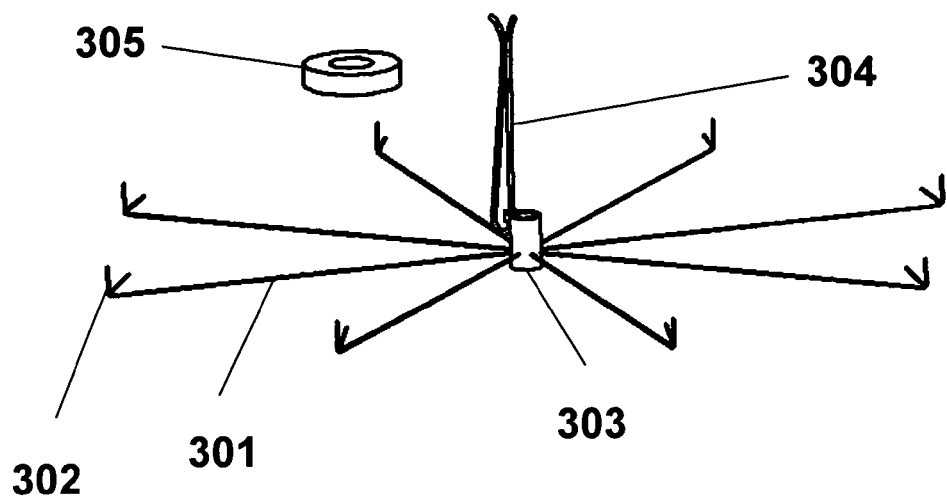
FIG. 3(a,b) is a schematic depiction of a vascular closure apposition device with a guidewire lumen, according to the present invention.
Figure 3B:
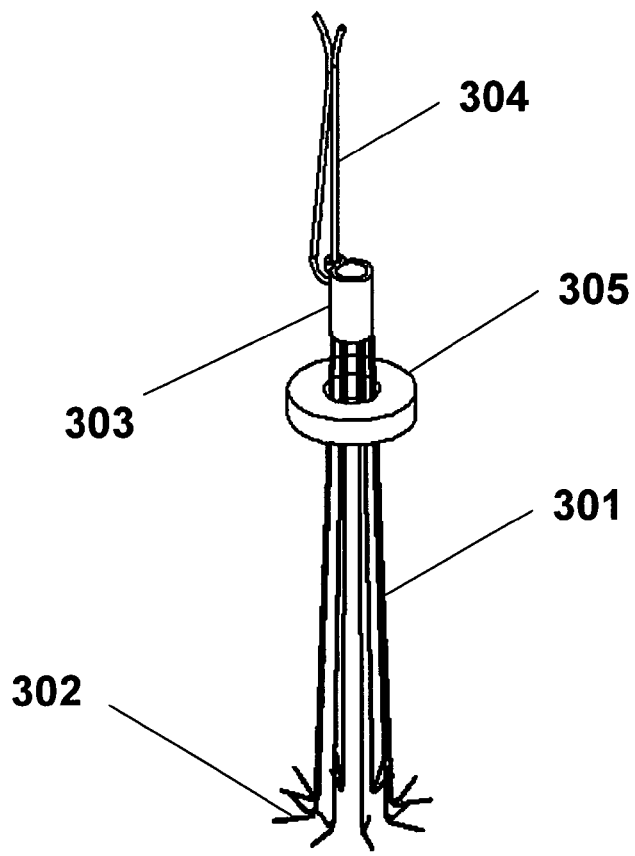

FIG. 3(*a,b*) is a lateral view of a vascular closure apposition umbrella with a guidewire lumen. The device comprises members 301 disposed substantially radially about a central junction 303. Each arm 301 comprises a tissue engagement structure 302, in the figure shown as a double hook on the end of the arm 301. The central junction 303 comprises a columnar guidewire lumen with a recovery loop or device for engaging a closed loop of string or suture 304. A retaining lock 305 that closes the device. FIG. 3(*b*) shows the device in a closed position with the retaining lock 305 engaged.

The embodiment of FIG. 3(*a,b*) comprises a closure apposition umbrella with a guidewire lumen. Inclusion of a guidewire lumen can reduce interference of the guidewire with placement of the umbrella, and allows the guidewire to remain in place in case the seating of the device is not optimal and then the device must be retrieved. The device can be delivered and placed with a guidewire in place. The apposed tissue might close the lumen once the guidewire is withdrawn. If desired, a soft one-way flap valve (not shown) or other structure can be placed in the lumen to occlude any blood flow that might occur when the wire is withdrawn.

Figure 4:
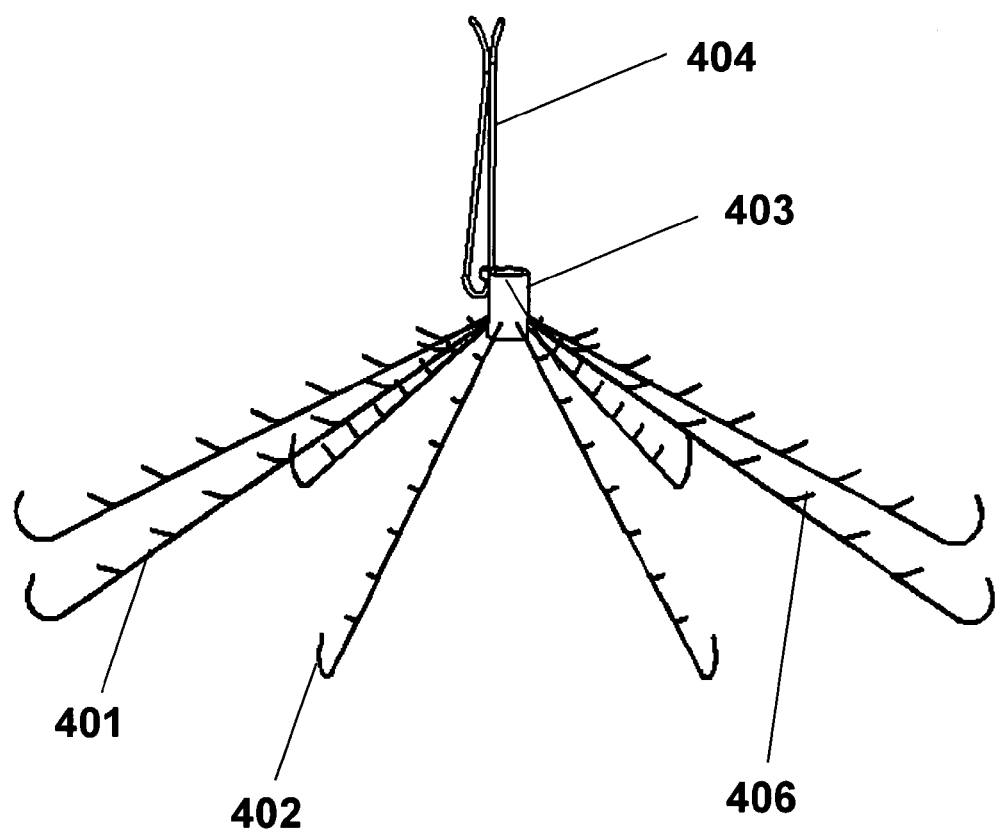
FIG. 4 is a schematic depiction of a vascular closure apposition device according to the present invention.

FIG. 4 is a lateral view of a vascular closure apposition umbrella comprising members 401 disposed substantially radially about a central junction 403, forming an overall conical shape. The members have tissue engagement structures 402, shown in the figure as hooks at the ends of the members 401. The members also have reversed barbs or feathers 406 to prevent intravascular migration of the device and to maintain the members in a closed state by engaging the tissue, a retaining lock, or both. In operation, the embodiment of FIG. 4 is similar to those discussed previously.

Figure 5:
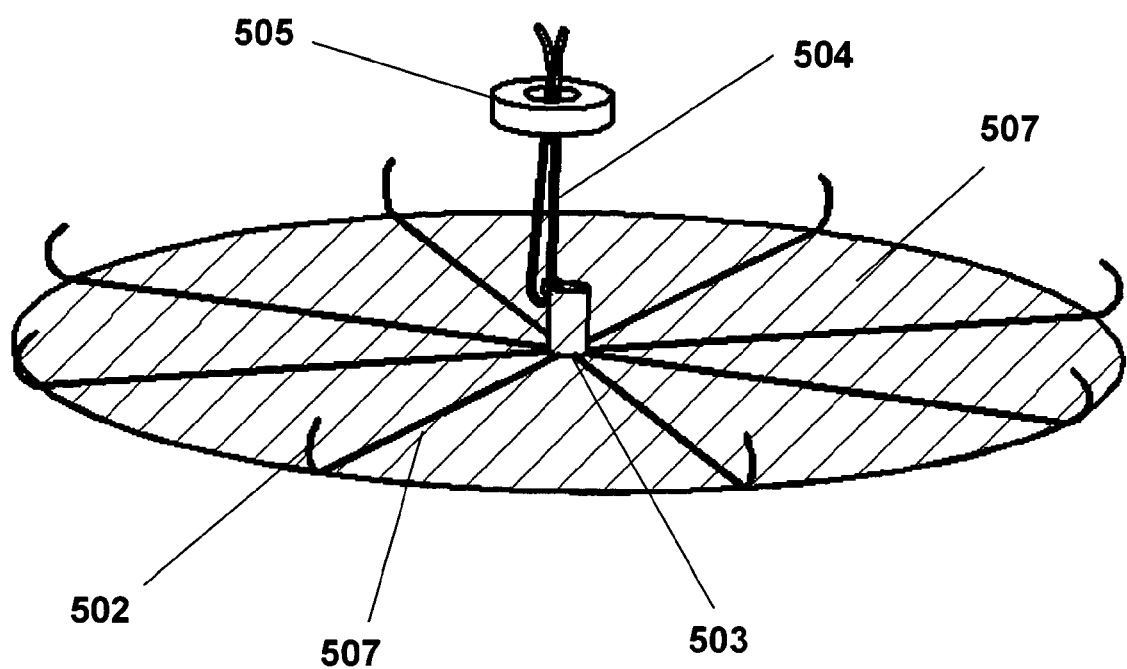
FIG. 5 is a schematic depiction of a vascular closure apposition device according to the present invention.

FIG. 5 is a lateral view of a vascular closure apposition umbrella. A plurality of members 501 are disposed substantially radially about a central junction 503. The members have tissue engagement structures 502, shown in the figure as a hook at the end of the member 502. The central junction 503 can have a recovery loop or device, and can engage a string or suture 504 for delivery, placement, and recovery. A retaining lock 505 can engage the members 501, the central junction 503, or both, to encourage the device to and maintain the device in a closed position. A backing or coating 507 can be mounted with the members as a fabric, web, or film. The backing can carry, or be made of, a material that can elute drug to prevent coagulation or to prevent endothelial hyperplasia or can be hemostatic initially, and fill the puncture track later.

Figure 6A:
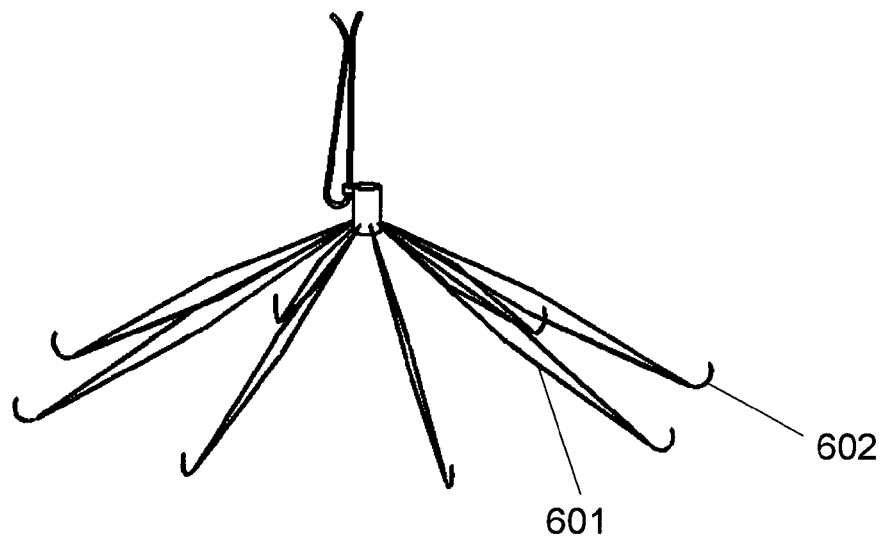
FIG. 6(a,b,c) are schematic depictions of example embodiments of vascular closure apposition devices according to the present invention.
Figure 6B:
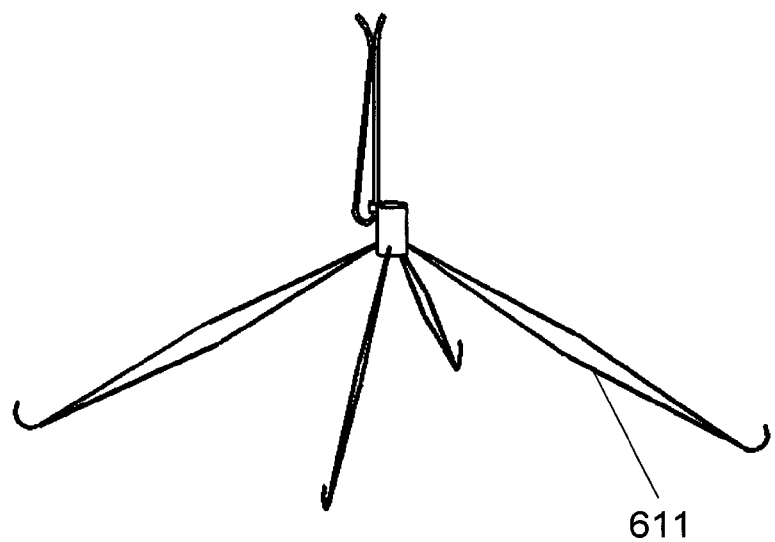
Figure 6C:
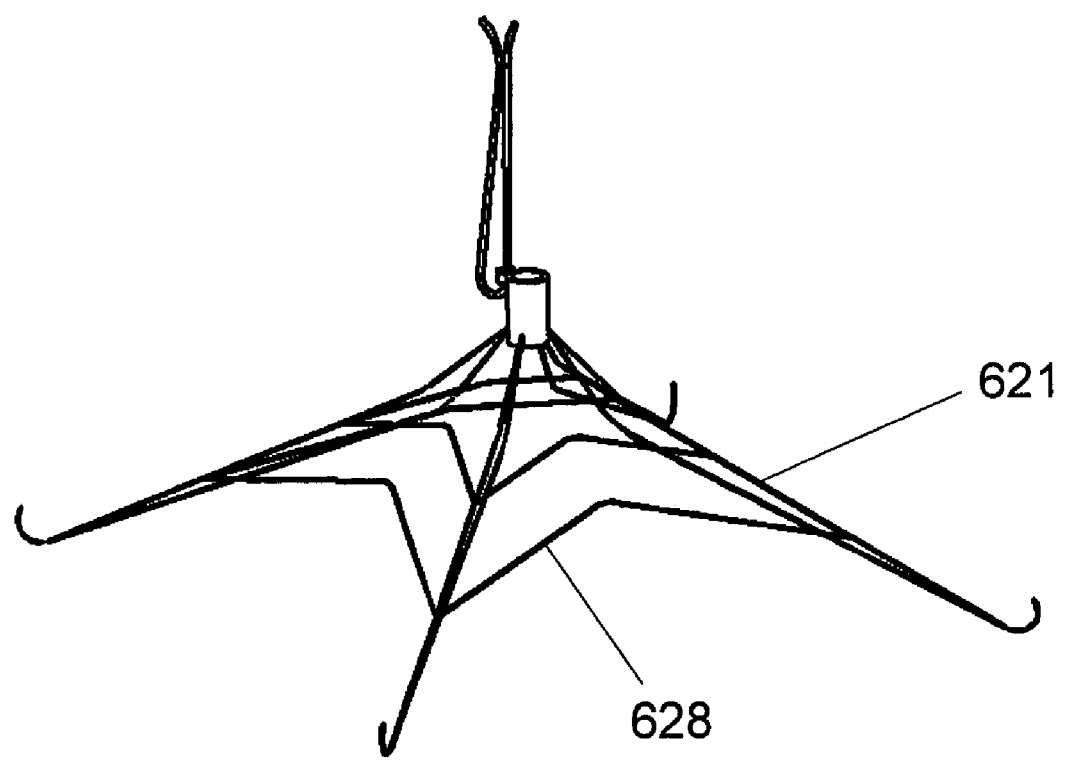
Figure 7A:
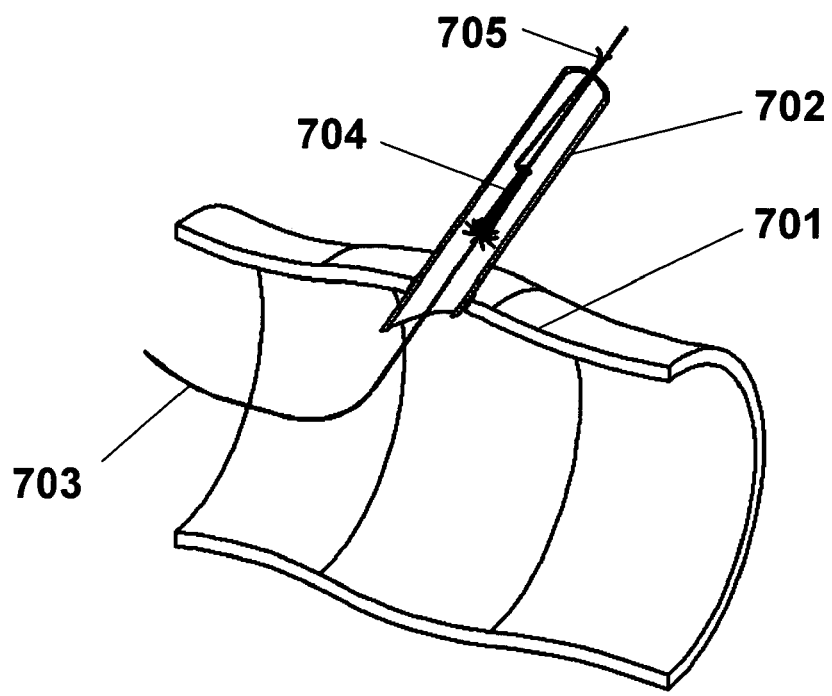
FIG. 7(a,b,c,d,e,f) is a schematic illustration of a method of closing a vascular opening according to the present invention.
Figure 7B:
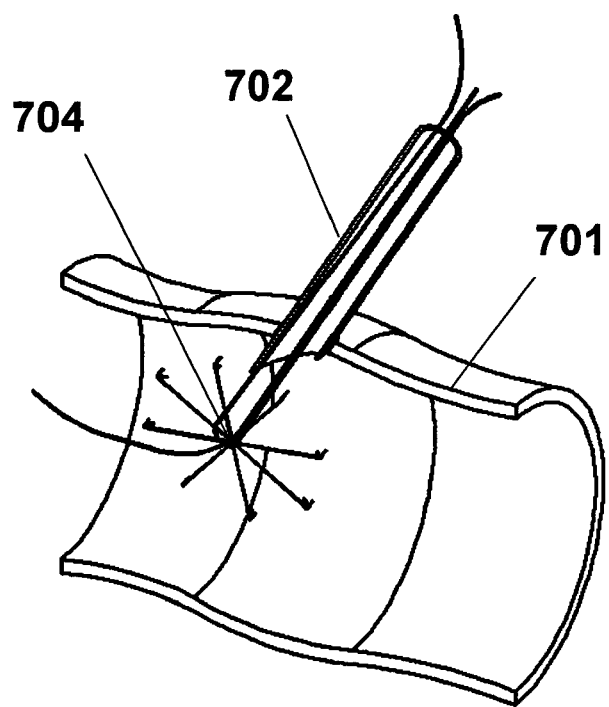
Figure 7C:
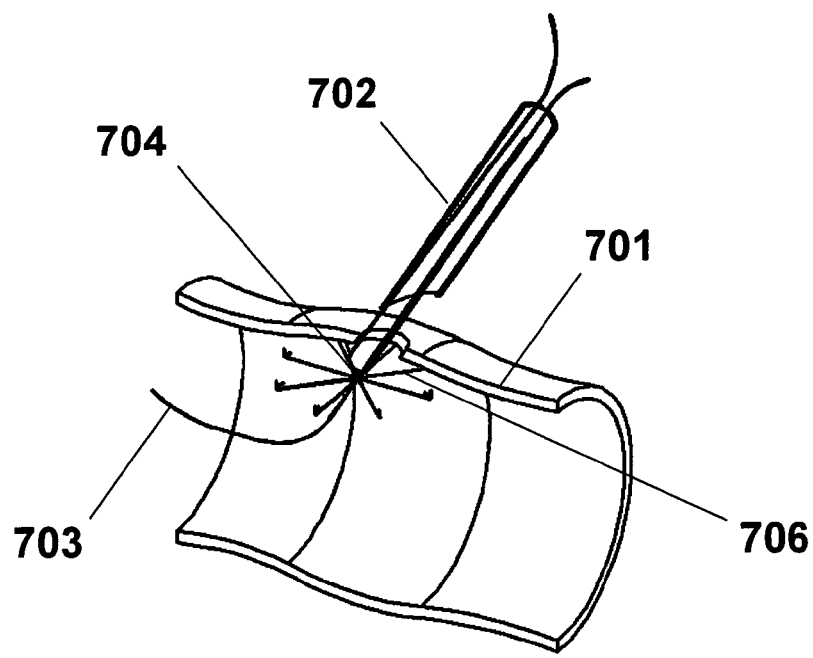
Figure 7D:
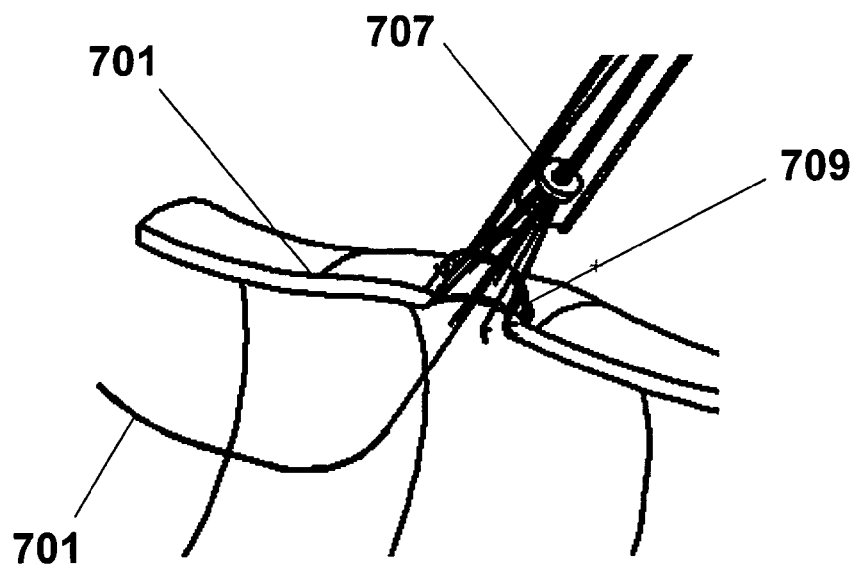
Figure 7E:
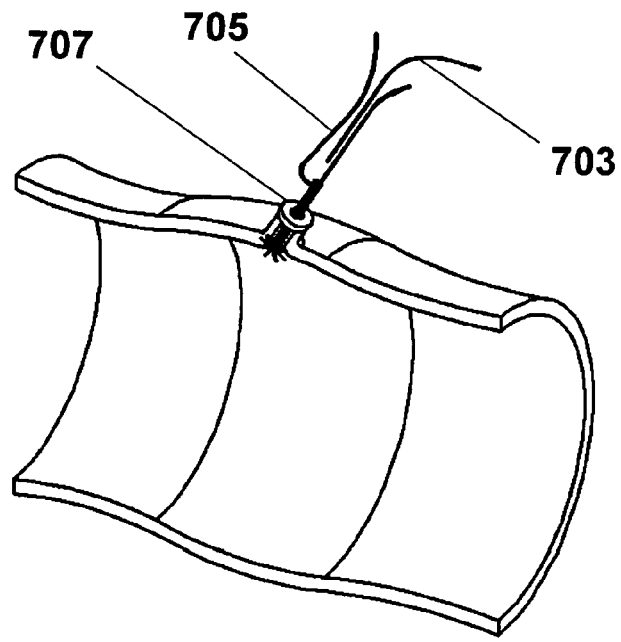
Figure 7F:
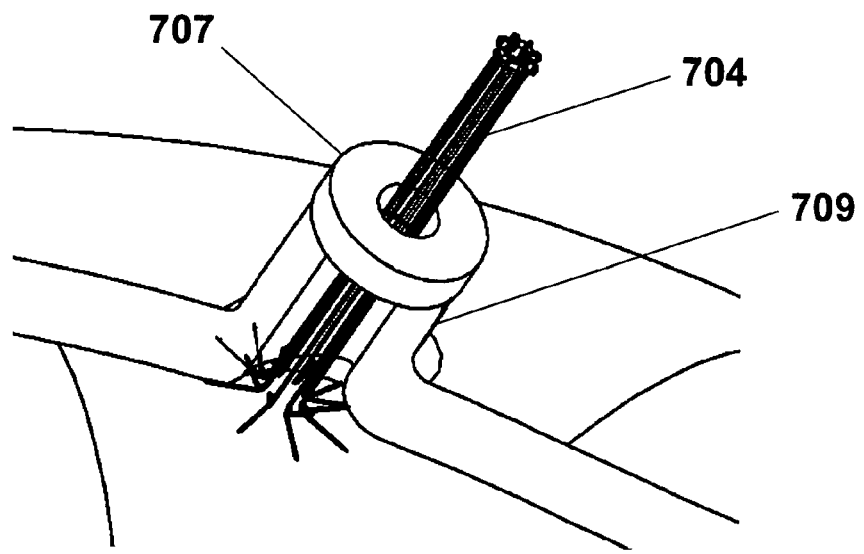

FIG. 6(*a,b,c*) are lateral views of example embodiments of vascular closure apposition devices according to the present invention. In FIG. 6(*a*), members 601 comprise elongated diamond shapes (rather than the straight wires depicted previously), which shape can have advantages in manufacture and in operation. The members 601 have tissue engagement structures 602, in the figure shown as hooks mounted with members at various locations. In FIG. 6(*b*), a device having a reduced number of members 611 is shown. A reduced number of members can provide for a simpler device, which can have manufacturing advantages and can be suitable for certain applications. In FIG. 6(*c*), members 621 comprise a non-linear geometry, and are connected by intermember struts 628. The non-linear geometry and intermember struts can allow specific opening and closing trajectories, and can allow optimization of forces when opening and closing. A wide variety of specific geometries and structures can be suitable with the present invention, as examples including geometries and structures currently used in vascular filters and stents.

FIG. 7(*a,b,c,d,e,f*) is a schematic illustration of a method of closing a vascular opening according to the present invention. A blood vessel 701 is penetrated by a sheath 702 and a guidewire 703. In FIG. 7(*a*), an apposition device 704, for example as described previously, is in a closed configuration within the sheath, with the loop of string or suture 705 engaged. In FIG. 7(*b*) the device 704 has been extruded from the sheath 702 and is in the expanded configuration within the vessel 701. In FIG. 7(*c*), the device 704 has been positioned against the wall of the vessel 701, seating the tissue engagement structures 706 in the tissue 701. The sheath 702 has been partially removed to facilitate seating of the device. The lock can be preseated on the device (not shown) or can be placed on the device after intravascular placement of the device by threading the lock down the guidewire or suture onto a central junction of the device after the device has been positioned in the blood vessel, or positioned by a separate sheath). In FIG. 7(*d*), a retaining lock 707 has been advanced over the members of the apposition device, forcing them into the closed configuration, and bringing the edges of the opening 709 together. If no bleeding occurs, then the guidewire 703 can be removed as shown in FIG. 7(*e*). The loop of string or suture 705 can be cut and removed, leaving the device 704 safely seated and locked with the opening closed, as shown in FIG. 7(*f*).

Delivery of the device can be done sequentially, or can be done with a dedicated device. For sequential delivery of the device, the following sequence of steps are suitable: 1) the guidewire and sheath are in place, 2) the device is pushed down the sheath, either next to the guidewire or with the guidewire in the lumen of the umbrella; 3) the umbrella is extruded, and then using the thread or suture, pulled tight against the lumen of the vessel; 4) the retaining lock is pushed down the thread and/or guidewire, and is pushed onto the umbrella while applying traction (the sheath can be removed partially at this stage); 5) after the retaining lock is seated, the sheath is observed for bleeding; 6) if there is no bleeding, then the sheath and guidewire are removed. For a dedicated device, there can be a sheath with the umbrella, a pushing device to push the umbrella out (another sheath), a sheath to push the retaining lock, and a thread/suture to oppose the other sheaths and to retrieve the umbrella if it is misplaced.

FIG. 8 (*a,b,c,d*) is a lateral view of a double-action vascular closure apposition device. In FIG. 8*a,* the unassembled device is in the closed position. The device comprises a plurality of umbrella members 801 disposed substantially radially about a central junction 803. Each umbrella member 801 can comprise a tissue hook 802, in the figure a double hook, spaced from the junction of the member and the central junction 803. The central junction 803 can include a central lumen for a guidewire, and is adapted to engage a plurality of opposite facing members 804, which opposite facing members can optionally have hooks, tissue penetrators, or feet. The opposite facing members can comprise memory material, and be configured such that they force a retaining lock 805 over the open umbrella members 1 (shown open in FIG. 8*c*) forcing them to close (as shown in FIG. 8*d*).

A closed loop of string or suture (not shown) can be joined to the device by ways of a lumen or loop. FIG. 8*a* shows the device preassembly. In FIG. 8*b,* the device is in assembled form and in a closed position, where the central junction 3 has passed through the retaining lock 805. In this form the double action vascular closure apposition device can reside within a delivery catheter before being placed in the puncture wound of a blood vessel. FIG. 8*c* shows the device partially expelled from the sheath (not shown), where the umbrella members 801 have opened and engaged the vessel wall, analogous to the embodiments previously described. In the arrangement of FIG. 8*c,* the opposite facing members 804 are retained in the sheath so that they are prevented from forcing the lock 805 over the umbrella members 801. FIG. 8*d* shows the device completely expelled from the delivery sheath, where the opposite facing members 804 are now forcing the retaining collar or lock 805 down the umbrella members 801, causing the portions of the umbrella members 801 with tissue engagement features (hooks in the figure) together (i.e., closing of the umbrella). The opposite facing members 804 are shown for ease of illustration as wire-like; they can be configured as coiled or semi-coiled structures, strut-like, multiple angles, spring-like, curled in an opposite direction, single or multiple members, elbow-like, or other geometrical or curvolinear shapes that when extended are neutral to the retaining lock, but when expelled, force the lock over the umbrella members, initiating closure.

Accordingly, the double action vascular closure apposition device of FIG. 8 is first closed, then opens, and then closes again, the second closure occurring spontaneously by contraction of the opposite facing members against the retaining lock. After the device has been delivered and vascular closure is complete, then the guidewire can be removed.

Figure 9A:
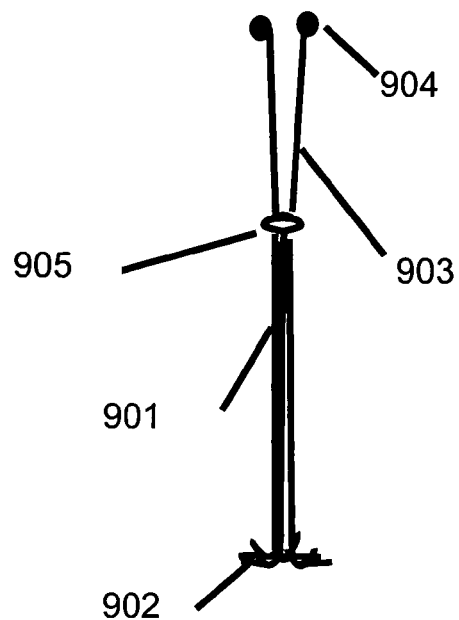
FIG. 9(a,b,c) is a schematic depiction of a double-action vascular closure apposition device according to the present invention.

FIG. 9 (*a,b,c,*) is a lateral view of a collarless double-action vascular closure apposition device. FIG. 9*a* shows the device in the closed position. A plurality of umbrella members 901 are disposed substantially radially about a central junction 905, which can have a lumen for a guidewire. The central junction can comprise a retaining ring which permits the members to flex along their length. Each of the umbrella members 901 has a tissue engagement feature spaced apart from the central junction 905, in the figure a double hook 902. The central junction is adapted to engage a plurality of opposite facing members 903, which optionally can have hooks, tissue penetrators, or feet 904. The opposite facing members 904 can be composed of memory material, and can be directly joined to a corresponding umbrella member, with the memory forces in the opposite facing members dominant over the memory forces in the umbrella members. FIG. 9a depicts the form that the collarless double action vascular closure apposition device would have while within a delivery catheter before being placed in the puncture wound of the blood vessel.

Figure 9B:
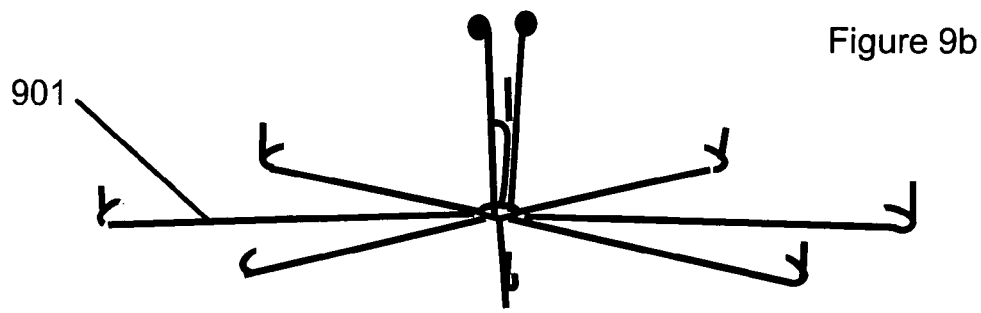
Figure 9C:
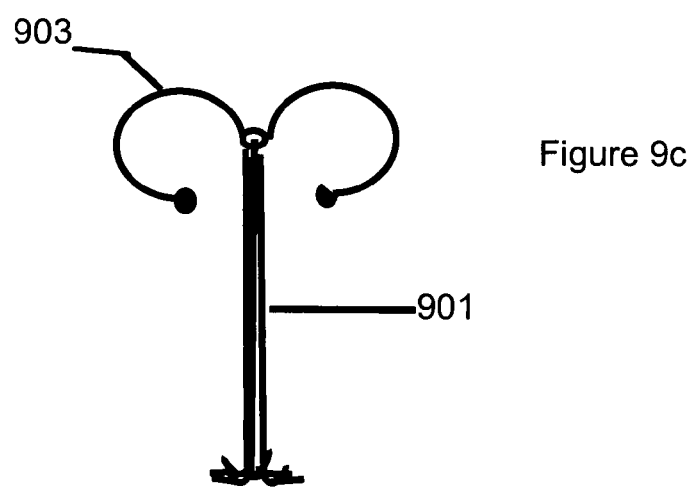

FIG. 9b shows the device partially expelled from the sheath (not shown). The umbrella members 901 have opened and engaged the vessel wall, analogous to embodiments described previously. The opposite members are still in the closed form, restrained there by the sheath. FIG. 9c shows the device completely expelled from the delivery sheath, where the opposite facing members 903 have curled or contracted. Since the opposite facing members are directly joined to the umbrella members and have dominant memory characteristics, they force the umbrella members 901 to close. The opposite facing members are shown in figure as wire-like for ease of illustration; they can be configured as coiled or semi-coiled structures, strut-like, multiple angles, spring-like, curled in an opposite direction, more than two members, elbow-like, or other geometrical or curvolinear shapes that when extended are neutral to the umbrella members, but when expelled, dominate over the umbrella members, and force closure of the umbrella members, initiating puncture wound closure.

Accordingly, the collarless double action vascular closure apposition device is first closed, then opens, and then closes again, with the second closure occurring spontaneously, by contraction of the opposite facing members which have dominant memory characteristics over the umbrella members. The central junction can be loose enough (e.g., made of a flexible polymer) to permit the forces from the contraction of the opposite facing members to be exerted on the umbrella members. In some embodiments each opposite facing member can be continuous with a corresponding umbrella member (i.e., a first portion of a single wire comprises an umbrella member, a second portion of the same wire comprising an opposite facing member). For simplicity, only two opposing members are shown in the figure; in embodiments where an umbrella member and a opposite facing member are formed from a single wire, the number of umbrella members can equal the number of opposite facing members, and each opposing member-umbrella member can be an integrated piece of memory material. After the device has been delivered and vascular closure is complete, then the guidewire can be removed.

In any of the embodiments described, the umbrella-like structure, members of this structure or components of the umbrella can be made from any number of suitable materials, including radioopaque materials and materials coated to be made radioopaque, including bioabsorbable polymers or compounds, non-absorbable alloys and compounds including stainless steel, MP35, Nitinol, Nickel-Titanium ally, Kevlar, nylon polyester acrylic, gold, platinum, tantalum, niobium, molybdenum, rhodium, palladium silver, hafnium, tungsten, iridium. Materials with memory would also be preferable to allow the umbrella to spontaneously open after placement by the sheath. These can be made in the form of wires, fibers, filaments, small beams, and other extruded, woven, or formed shapes. Piano wire, super elastic memory wire, chromium allows, alloys of titanium and nickel, and other elastic memory materials previously mentioned as well as others can be used as well The umbrella fabric can be made from a number of suitable materials, including flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, co-polymers of these or other polymers, or drug-embedded or drug-eluting polymers to prevent coagulation or intimal hyperplasia (such as Taxol), also which can be made radioopaque by markers and addition of appropriate radiopaque materials.

EXAMPLE EMBODIMENTS

The present invention can comprise a device to close puncture wounds caused by catheter procedures and especially angiography comprised of an expandable umbrella-like device that in the compressed state resides in a sheath, and after being expelled from the sheath assumes a planar or conical or other shape, engages vessel wall by means of tissue hooks or penetrators, is collapsed, analogous to umbrella tines, and brings the edges of the vessel wound or puncture into apposition. The device can have a retaining locking device that prevents the umbrella-like structure from reopening. This locking can be achieved by mechanical means including deformable enlargements on the members, dentates, male-female connectors, peg and hole, or other directional mating/locking devices on the members and retaining locking device. This locking device can have a washer like appearance, but can also take a number of different forms, including an inverted umbrella device made of metal, plastic, composites, or biodegradable material.

The device can have single or multiple hooks and penetrating devices to engage and seize the vessel wall. Each hook can be a single or multiple hook. The device can have members (or tines) of the umbrella-like structure that are linear, curvilinear, spiral, leaf-like, diamond shaped, woven, or other complex shapes, but still function as an opening-closing structure that can accommodate a retaining lock. The device when expanded can have a planar or conical or reverse conical geometry, or other complex shape that can collapse into near-linear form with traction and locking of the retaining lock. The device can have a retrieval fitting, usually a loop, fitted with a closed loop thread, string, or suture in order to apply traction to the device. The device can have a lumen for a guidewire.

The device can have members that are coated or backed with a fabric or membrane, either completely or partially. The device can elute therapeutic material to prevent thrombogenesis, hemorrhage, inflammation, and intimal hyperplasia with vascular closure. The device can be used in angiography, angioplasty, vascular puncture, tissue biopsy, or trauma that cause a puncture wound that should be closed. The device can comprise materials with memory, so that the device spontaneously assumes it therapeutic shape when expelled from the sheath. The device can comprise at least 2 or more members; 3 or more members can be preferable in some applications. The device can have members with angled dentates or tissue penetrators to prevent movement or migration of the device into the lumen of the blood vessel. These can also be used to retain the retaining lock.

A tissue opening can be closed according to the present invention by a) introducing a guidewire and sheath, b) penetrating the proximal surface of the blood vessel by the sheath and the guidewire, c) placing a device in the closed form in the sheath, with the loop of string or suture, d) extruding the device from the sheath and expanding while in the tissue (e.g., while inside a blood vessel), e) pulling the device against the tissue wall (e.g., the blood vessel wall), seating the hooks in the tissue, f) partially removing the sheath is to seat the device while a retaining lock is advanced, g) advancing the retaining lock over the members of the device while applying traction with the string, forcing them in the closed position, h) bringing the edges of the puncture wound together; if no bleeding occurs, i) then removing the guidewire, j) cutting the loop of string, leaving the device safely seated and locked with the puncture repaired.

A tissue opening can be closed according to the present invention with sequential delivery of a device. For example, the following steps can be taken 1) first the guidewire and sheath are in place, 2) next the umbrella is pushed down the sheath, either next to the guidewire or with the guidewire in the lumen of the umbrella; 3) the umbrella is extruded, and then using the thread or suture, pulled tight against the lumen of the vessel; 4) next the retaining lock is pushed down the thread and/or guidewire, and is pushed onto the umbrella while applying traction (the sheath can be removed partially at this stage, 5) after the retaining lock is seated, the sheath is observed for bleeding, 6) if there is no bleeding, then the sheath and guidewire are removed.

A tissue opening can be closed according to the present invention employing a dedicated device consisting of a sheath containing a device, a pushing device to push the device out (e.g., another sheath), a sheath to push the retaining lock, and a thread/suture to oppose the movement of the other sheaths and to retrieve the umbrella if it is misplaced.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

The invention claimed is:

1. A method of closing an opening in tissue having a proximal surface using a device having a plurality of tissue engagement elements extending distally from a central junction and capable of occupying a plurality of compressed configurations and at least one expanded configuration and a separate locking element, said method comprising the steps of:
   passing the device while in a first one of the compressed configurations through a sheath disposed adjacent to an opening in the proximal surface of the tissue;
   expelling the device from the sheath into space beyond the proximal surface of the tissue such that the device assumes the at least one expanded configuration;
   manipulating the device such that the tissue engagement elements engage the tissue;
   following engaging the tissue with the tissue engagement elements, advancing the locking element along a flexible member from a proximal end of the flexible member toward the device and along the plurality of tissue engagement elements, the flexible member extending from a device proximal end at the central junction to a position remote from and proximal to the device proximal end; and
   moving the device to bring edges of the opening into apposition.

2. The method of claim 1, further comprising a step of maintaining the device in a second one of the compressed configurations after bringing the edges of the opening into apposition.

3. The method of claim 2, wherein the second compressed configuration is expanded relative the first compressed configuration.

4. The method of claim 3, wherein the at least one expanded configuration is expanded relative to the second compressed configuration.

5. The method of claim 4, wherein the at least one expanded configuration defines a planar or conical shape.

6. The method of claim 1, wherein the device includes a receiving element adapted to engage the flexible member and wherein said maintaining step comprises applying tensile force on the flexible member opposed to the force on the locking element to cause the device to occupy the second compressed configuration.

7. The method of claim 1, wherein said moving step comprises applying traction to the device.

8. The method of claim 7, wherein said manipulating step comprises pulling the flexible member to bias the device towards the tissue.

9. The method of claim 8, wherein the moving step causes the device to occupy a second one of the compressed configurations.

10. The method of claim 9, further comprising the steps of passing the flexible member through the locking element, passing the locking element down the flexible member to the device, pulling the flexible member such that a portion of the device engages the locking element and causes the device to assume the second compressed configuration.

11. The method of claim 1, wherein the locking element defines a lumen and further comprising the step of passing a guidewire through the lumen.

12. The method of claim 11, further comprising the step of observing the sheath for bleeding after the locking element is seated and then removing the sheath and guidewire if no bleeding is observed.

13. The method of claim 1, wherein said manipulating step comprises pulling the flexible member coupled to the tissue engagement elements to bias the device towards the tissue.

14. The method of claim 1, wherein the opening in tissue comprises an external opening in a blood vessel.

15. The method of claim 14, wherein the opening comprises a vascular puncture wound.

16. The method of claim 1, wherein said passing step comprises passing the device while in a first one of the compressed configurations through the sheath extending through the opening in the proximal surface of the tissue.

17. A method of closing an opening in tissue having a proximal surface using a device having a plurality of tissue engagement elements extending distally from a central junction and capable of occupying a plurality of compressed configurations and at least one expanded configuration, each tissue engagement element include one or more tissue engagement structures, said method comprising the steps of:
   locating a sheath within the opening in the tissue, the sheath receiving a guidewire;
   passing the device while in a first one of the compressed configurations through a sheath disposed adjacent to an opening in the proximal surface of the tissue;
   expelling the device from the sheath into space beyond the proximal surface of the tissue such that the device assumes the at least one expanded configuration with the plurality of tissue engagement elements extending generally perpendicularly from the central junction of the device;
   with a flexible member extending proximally from the central junction of the device, manipulating the device to engage the tissue with the one or more tissue engagement structures of the tissue engagement elements; and
   following engaging the tissue, advancing a locking element on the flexible member and along the plurality of tissue engagement element to move the device to bring edges of the opening into apposition.

18. The method of claim 17, further comprising the step of passing the locking element along the guidewire to the device.

19. The method of claim 17, further comprising the step of passing the locking element along the flexible member to the device.

20. The method of claim 17, further comprising the step of maintaining the device in a second one of the compressed configurations after bringing the edges of the opening into apposition.

21. The method of claim 20, wherein the second compressed configuration is expanded relative the first compressed configuration.

22. The method of claim 17, wherein each tissue engagement element of the plurality of tissue engagement elements includes an angularly orientated tissue engagement structure and a tissue engagement structure extending generally perpendicularly from the tissue engagement element, the step of manipulating the device further comprises the step of engaging the angularly orientated tissue engagement structure and the tissue engagement structure into the tissue.

23. The method of claim 17, wherein the step of advancing further comprising passing the locking element over the central junction.

24. A method of closing an opening in tissue having a proximal surface using a device having a plurality of tissue engagement elements extending distally from a central junction and capable of occupying a plurality of compressed configurations and at least one expanded configuration and a separate locking element, each tissue engagement element include one or more tissue engagement structures, said method comprising the steps of:
   passing the device while in a first one of the compressed configurations through a sheath disposed adjacent to an opening in the proximal surface of the tissue;
   expelling the device from the sheath into space beyond the proximal surface of the tissue such that the device assumes the at least one expanded configuration with the plurality of tissue engagement element extending generally perpendicularly from the central junction of the device;
   with a flexible member extending proximally from the central junction of the device, manipulating the device to engage the tissue with the one or more tissue engagement structures of the tissue engagement elements; and
   following engaging the tissue, advancing the locking element along a flexible member from a proximal portion of the flexible member toward the device, the flexible member extending from a device proximal end to a position remote from and proximal to the device proximal end; and
   moving the locking member along the plurality of tissue engagement elements of the device to bring edges of the opening into apposition.

25. The method of claim 24, further comprising a step of locating a guidewire and sheath in the opening of the tissue.

26. The method of claim 25, further comprising removing the guidewire and sheath from the opening following opening closure.

27. The method of claim 26, further comprising applying traction to the device while moving the locking member relative to the plurality of tissue engagement elements.

* * * * *